(12) United States Patent
Yoshida et al.

(10) Patent No.: US 8,982,357 B2
(45) Date of Patent: Mar. 17, 2015

(54) IMAGING DEVICE AND IMAGING METHOD

(75) Inventors: Hirofumi Yoshida, Yokohama (JP);
Kenji Muto, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 316 days.

(21) Appl. No.: 13/320,644

(22) PCT Filed: May 19, 2010

(86) PCT No.: PCT/JP2010/058848
§ 371 (c)(1),
(2), (4) Date: Nov. 15, 2011

(87) PCT Pub. No.: WO2010/134624
PCT Pub. Date: Nov. 25, 2010

(65) Prior Publication Data
US 2012/0062901 A1 Mar. 15, 2012

(30) Foreign Application Priority Data

May 22, 2009 (JP) ................................ 2009-124274
Mar. 31, 2010 (JP) ................................ 2010-082803

(51) Int. Cl.
*G01B 9/02* (2006.01)
*G01N 21/47* (2006.01)
*A61B 3/10* (2006.01)
*A61B 5/00* (2006.01)
*G01N 21/17* (2006.01)

(52) U.S. Cl.
CPC ............ *G01N 21/4795* (2013.01); *A61B 3/102* (2013.01); *A61B 5/0066* (2013.01); *A61B 5/0073* (2013.01); *G01B 9/02044* (2013.01); *G01B 9/02027* (2013.01); *G01B 9/02091* (2013.01); *G01B 9/02058* (2013.01); *G01N 2021/1787* (2013.01); *G01B 2290/70* (2013.01); *G01B 2290/35* (2013.01)
USPC ....................................................... 356/479

(58) Field of Classification Search
CPC ........... G01B 9/02027; G01B 9/02044; G01B 9/02058; G01B 9/02091; G01B 2290/35; G01B 2290/70; G01J 3/0294; G02B 6/4226; A61B 3/102; A61B 5/0066
USPC ................. 356/479, 497; 250/227.19, 227.27
See application file for complete search history.

(56) References Cited

U.S. PATENT DOCUMENTS

2006/0124840 A1* 6/2006 Ida et al. ........................ 250/226
2008/0285043 A1 11/2008 Fercher

FOREIGN PATENT DOCUMENTS

| CN | 1539376 A | 10/2004 |
|---|---|---|
| CN | 1721840 A | 1/2006 |
| JP | 08-252256 A | 10/1996 |
| JP | 2875181 B2 | 3/1999 |
| JP | 2008-508068 A | 3/2008 |
| JP | 2008-541989 A | 11/2008 |
| JP | 2009-518088 A | 5/2009 |
| WO | 2006-015717 A1 | 2/2006 |

OTHER PUBLICATIONS

Baumann, Bernhard et al. "Single camera based spectral domain polarization sensitive optical coherence tomography". Optics Express, vol. 15, No. 3, Feb. 5, 2007, pp. 1054-1063.*

* cited by examiner

*Primary Examiner* — Michael A Lyons
(74) *Attorney, Agent, or Firm* — Canon U.S.A. Inc., IP Division

(57) ABSTRACT

The present invention relates to a structure in which a sensor includes a first area and a second area upon which dispersed first and second lights are focused. The first and second areas are disposed in a dispersion direction or a direction perpendicular to the dispersion direction. A distance between the first and second areas is adjusted by using a distance between a plurality of fiber ends from which a plurality of combined lights exit and an optical magnification at a detecting section.

21 Claims, 12 Drawing Sheets

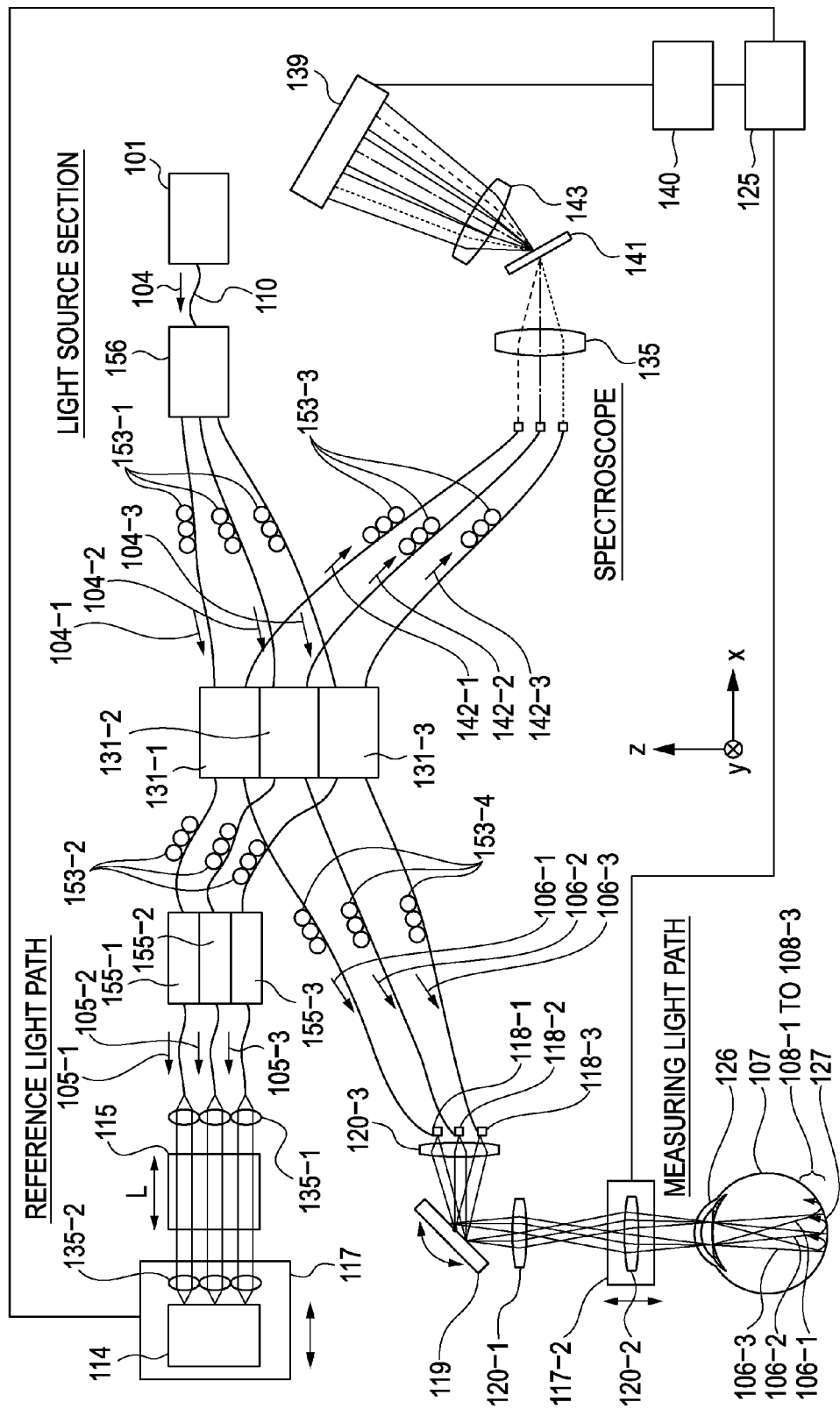

132

IMAGING DEVICE AND IMAGING METHOD

TECHNICAL FIELD

The present invention relates to an imaging device using optical coherence tomography, an imaging method, and medical equipment used in observing, for example, the fundus of an eye or skin.

BACKGROUND ART

In recent years, an imaging device (hereunder may also be referred to as an "OCT device") using optical coherence tomography (OCT) making use of coherence of low coherence light has been put into practical use.

The OCT device can obtain a high-resolution tomographic image by irradiating a sample with measuring light and by causing back-scattered light (returning light) from the sample to interfere with reference light. Therefore, a tomographic image of the retina in the fundus of a detection eye is obtained, so that the OCT device is widely used in, for example, ophthalmological examination of the retina.

Here, two types of OCT method are primarily available, that is, time domain-OCT (TD-OCT) and Fourier domain-OCT (FD-OCT). The FD-OCT is a method in which spectrum information is subjected to Fourier transformation, to obtain together pieces of intensity information corresponding to depth-direction positions. Therefore, the FD-OCT can obtain a tomographic image at a higher speed than the TD-OCT in which a coherence gate position is changed for obtaining a depth-direction position.

In OCT measurements in, for example, ophthalmological examination of the retina, a tomographic image may be displaced or may be missing due to eyeball movement (typically, involuntary eye movement). In particular, since it takes time to obtain a tomographic image when a measurement is carried out at a wide angle of view, the probability that the tomographic image is displaced or that the tomographic image is missing is increased.

Accordingly, Japanese Patent No. 2875181 (Patent Document 1) discusses a method that uses a plurality of beams and that narrows a measurement area per one beam to reduce the measurement time. In Patent Document 1, an interferometer that separates nine beams into measuring lights and reference lights is used. The interference lights obtained from the respective beams are dispersed, and the dispersed interference lights are detected with the same two-dimensional sensor array provided for the plurality of beams.

Polarization OCT for carrying out OCT measurement with one spectroscope by obtaining a plurality of interference lights having different polarization states is discussed in "Single Camera Based Spectral Domain Polarization Sensitive Optical Coherence Tomography," 2007/Vol. 15, No. 3/Optics Express 1054. By this, two interference lights are obtained with one line sensor in one spectroscope so that the size of the device is reduced. The method that uses a plurality of beams and that narrows a measurement area per one beam is not discussed in the document.

CITATION LIST

Patent Literature

PTL1 Japanese Patent No. 2875181

Non Patent Literature

NPL1 Single Camera Based Spectral Domain Polarization Sensitive Optical Coherence Tomography, 2007/Vol. 15, No. 3/Optics Express 1054

SUMMARY OF INVENTION

By, for example, thermal flickering of a light source itself, light generated from the light source generates light having wavelength widths that are larger than an intended wavelength width.

Therefore, in Japanese Patent No. 2875181, in order to prevent a plurality of dispersed interference lights from being superimposed upon each other on the two-dimensional sensor array, the distances between areas where the respective interference lights are detected are made sufficiently large. This is because, when the plurality of interference lights are superimposed upon each other on the sensor, crosstalk occurs between the interference lights, thereby generating noise in a resulting tomographic image that is obtained.

Here, since it is necessary for the detection areas to be sufficiently separated apart from each other, pixels that are not used for the detection are provided. Therefore, the number of pixels required for the two-dimensional array sensor is increased, thereby reducing read-out speed.

How large the distances between the beams that focus on the sensor should be is not discussed or even suggested. Therefore, the distances discussed in Japanese Patent No. 2875181 are thought to be larger than necessary.

In "Single Camera Based Spectral Domain Polarization Sensitive Optical Coherence Tomography," 2007/Vol. 15, No. 3/Optics Express 1054, the distance between two interference lights that focus on a line sensor is not discussed or even suggested. If the beams that are focused are not separated from each other, crosstalk also occurs between the beams.

An imaging device using optical coherence tomography according to the present invention includes a light source configured to generate light; a splitting section configured to split the light from the light source into reference light and measuring light; a scanning optical section configured to scan an examination object with the measuring light; and a detecting section configured to detect combined light in which the reference light and returning light from the examination object are combined with each other. The examination object is scanned with a plurality of the measuring lights used to scan the examination object. The detecting section includes a dispersing element and a sensor, the dispersing element being configured to disperse a plurality of the combined lights, the sensor being configured to detect the plurality of the combined lights that have been dispersed, the dispersed lights including a first dispersed light and a second dispersed light. The sensor includes a first area and a second area at which the first dispersed light and the second dispersed light are focused. The first area and the second area are disposed in a direction of the dispersion or in a direction substantially perpendicular to the direction of the dispersion. A distance between the first area and the second area is adjusted by using a distance between a plurality of fiber ends from where the plurality of the combined lights exit and an optical magnification at the detecting section.

Another imaging device according to the present invention includes a single dispersing unit configured to disperse a plurality of combined lights formed by combining a plurality of returning lights and a plurality of reference lights, the plurality of returning lights returning from an examination object illuminated by a plurality of measuring lights, the plurality of reference lights corresponding to the plurality of measuring lights; a dispersion-side illuminating unit configured to perform illumination with the plurality of combined lights at a substantially conjugate position with respect to the single dispersing unit and at an incident angle with respect to the single dispersing unit; a sensor configured to detect a plurality of lights based on the plurality of combined lights from the single dispersing unit; and an obtaining unit configured to obtain an optical coherence tomographic image of the examination object based on the plurality of lights detected at the sensor.

According to the present invention, it is possible to provide a structure in which the distances in the sensor between the plurality of interference lights that focus on the sensor are prescribed, to prevent crosstalk from occurring between the interference lights.

Further features of the present invention will become apparent from the following description of exemplary embodiments with reference to the attached drawings.

BRIEF DESCRIPTION OF DRAWINGS

FIGS. 1A and 1B are schematic views illustrating the structure of an imaging device using optical coherence tomography in first and second embodiments.

DESCRIPTION OF EMBODIMENTS

Figure 1B:
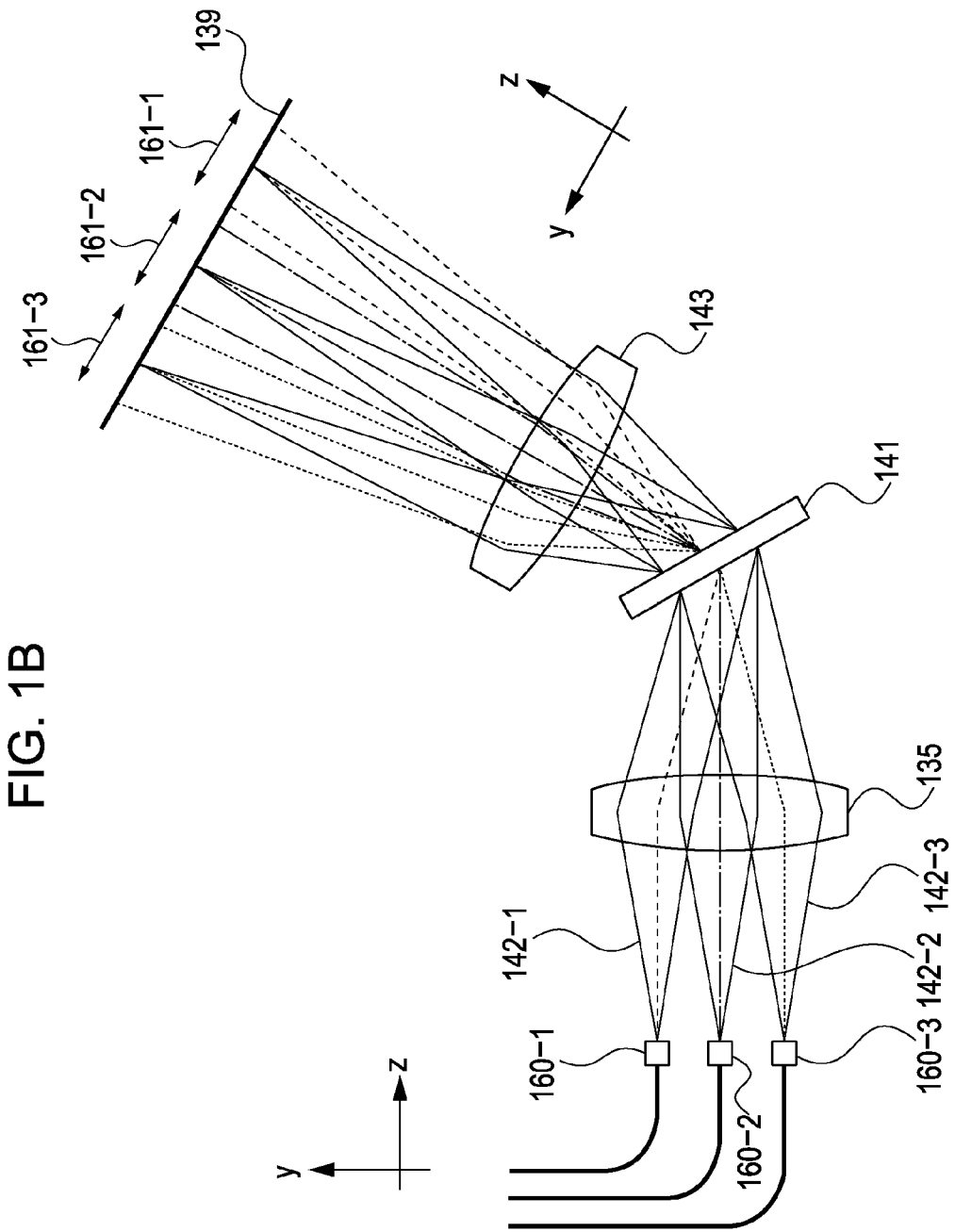

Preferred embodiments of the present invention will hereunder be described.

An imaging device using optical coherence tomography according to an embodiment of the present invention will be described with reference to FIGS. 1A and 1B.

First, reference numeral 101 denotes a light source for generating light (low coherence light). A super luminescent diode (SLD) can be applied to the light source 101. Amplified spontaneous emission (ASE) can also be applied to the light source 101. In addition, ultrashort pulse laser, such as titanium sapphire laser, can also be applied to the light source 101. Anything that can generate low coherence light may be applied to the light source 101. The wavelength of the light generated from the light source 101, though not particularly limited, is in the range of from 400 nm to 2 µm. A wavelength interval for realizing OCT may be, for example, 1 nm or more; desirably, 10 nm or more; and, more desirably, 30 nm or more.

Reference numerals 131 (reference numerals 131-1 to 131-3) denotes splitting sections that split the light from the light source 101 into reference lights and measuring lights. For example, a beam splitter or a fiber coupler may be applied to the splitting sections 131. Accordingly, anything that can split the light may be applied to the splitting sections 131.

Reference numeral 119 denotes a scanning optical section for scanning an examination object to be examined (examination eye 107 to be examined). For example, a galvano scanner is desirably used for the scanning optical section 119. However, anything that can scan an examination object with light may be used.

FIG. 1B shows a detecting section (spectroscope) for detecting combined lights of the reference lights and returning lights from the examination object 107. The detecting section includes a dispersing element for dispersing a plurality of combined lights 142 (142-1 to 142-3). The dispersing element 141 is, for example, a diffraction grating or a prism, and may be anything that can disperse the light. The detecting section includes a sensor 139 for detecting the plurality of lights dispersed by the dispersing element 141. The sensor 139 may be a line sensor, a two-dimensional sensor, or anything that can detect the light. Here, the plurality of combined lights 142 exit from a plurality of fiber ends 160 (160-1 to 160-3).

The examination object 107 can be scanned with the plurality of measuring lights used to scan the examination object 107. The method that a Michelson type interferometer uses for forming a plurality of measuring lights differs from the method that a Mach-Zehnder type interferometer uses for forming a plurality of measuring lights (described later).

The sensor 139 has first and second areas (for example, areas 161-1 to 161-3) where first and second lights that have been dispersed (for example, lights obtained after the plurality of combined lights 142 have passed through the dispersing element 141) are focused. Here, the first and second areas refer to areas (unit: pixels) where the sensor is irradiated with the plurality of dispersed lights.

Figure 6:
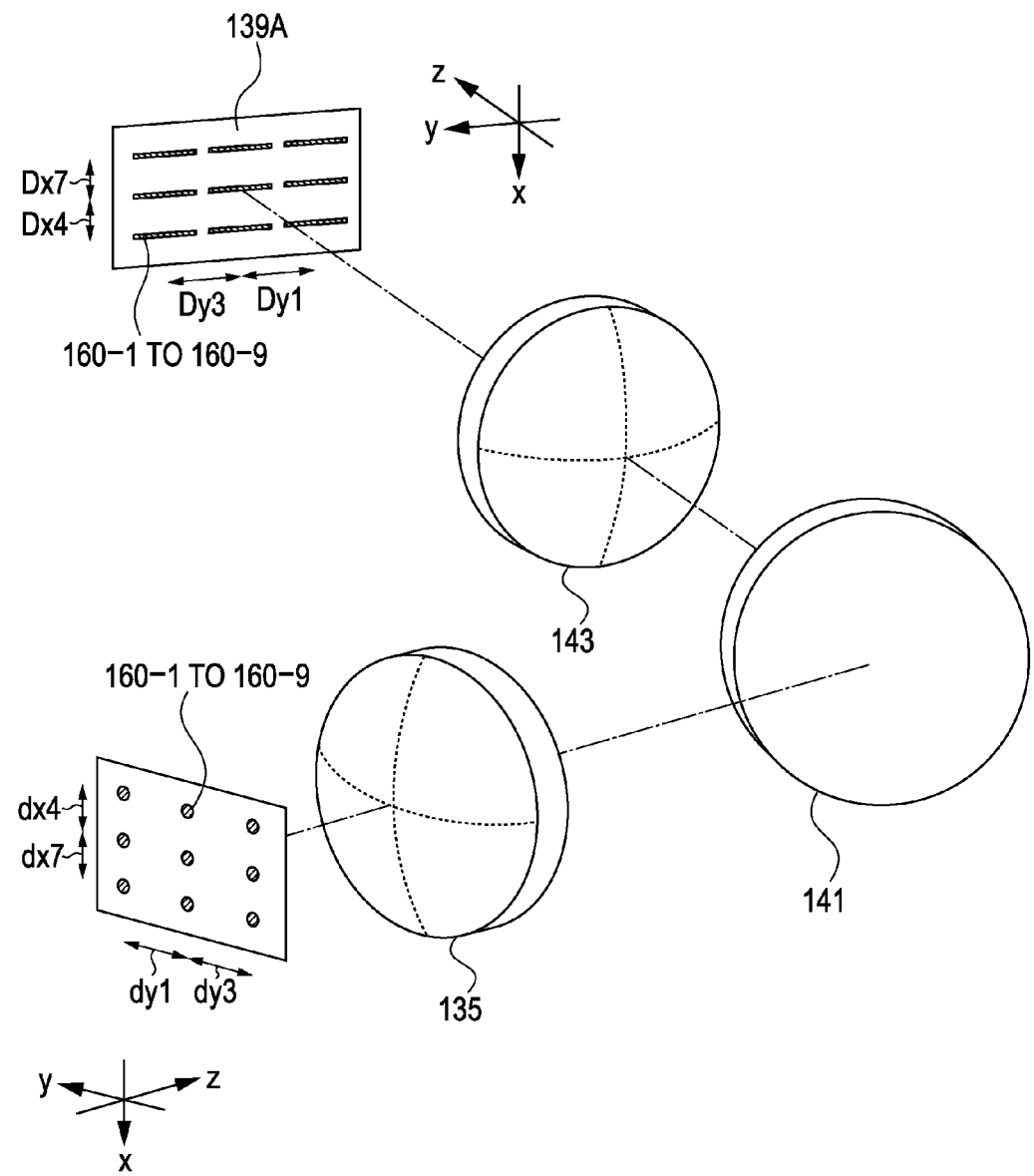
FIG. 6 is a schematic view illustrating the relationship between the positions of respective members in the structure of a spectroscope in a third embodiment.

The first and second areas are disposed in a direction of the dispersion (such as a y direction in FIG. 6), or in a direction substantially perpendicular to the dispersion direction (such as an x direction in FIG. 6).

Distances between the first and second areas (such as Dx and Dy in FIG. 6) are adjusted by using the distances between the plurality of fiber ends 160 from where the plurality of combined lights 142 exit and optical magnification (for example, determined by the ratio between the focal length of a lens 135 and a lens 143 included in the detecting section) at the detecting section.

This makes it possible to restrict crosstalk between the dispersed lights in the sensor 139. In addition, the first and second areas can be brought as close as possible. That is, the distances between the first and second areas (unit: pixels) can be made small (the number of pixels can be made small).

Here, it is desirable that the plurality of dispersed lights be focused at the respective areas 161.

If the first and second areas are disposed in the dispersion direction (such as the y direction in FIG. 6), it is desirable that the pixels in the second area at a first area side be disposed as follows. That is, the pixels are included in an area of the sensor 139 where, of the light that is focused on the first area, light having an intensity that is less than $10^{-4}$ times the intensity of light detected at the second area is detected.

If the first and second areas are disposed in the dispersion direction (such as the y direction in FIG. 6), and the sensor 139 includes a third area (see FIGS. 5A and 5B) disposed substantially perpendicularly to the dispersion direction (such as the x direction in FIG. 6) with respect to the first area, it is desirable that the following is true. That is, the distance between the first area and the third area is less than the distance between the first area and the second area.

It is desirable that a line sensor be provided so as to extend from the first to third areas (such as 161-1 to 161-9 in FIG. 6). It is desirable that, with regard to the relative positions of the fiber ends, at least a mechanism that can adjust the distances between the fiber ends (such as d1 and d3 in FIG. 3A) be provided.

Michelson Type Interferometer

If a Michelson type interferometer is used, the splitting sections 131 are formed so that the reference lights and the measuring lights are combined. That is, the splitting sections 131 are formed so as to split the light generated from the light source 101 into reference lights and measuring lights, and so as to combine the reference lights and returning lights.

Here, the splitting sections 131 split the light generated from the light source 101 into a plurality of lights, and split the plurality of split lights into reference lights and measuring lights.

Light is generated from a plurality of the light sources. The plurality of lights are split into reference lights and measuring lights.

Mach-Zehnder Type Interferometer

If a Mach-Zehnder type interferometer is used, a combining section for combining the reference lights and the measuring lights is provided. The combining section is a fiber coupler or anything else that can combine the lights.

Light generated from the light source 101 is split into the measuring lights and the reference lights, and the split measuring lights and the split reference lights are split into a plurality of lights.

Another Embodiment

Imaging Method

Here, in another embodiment, an imaging method using the imaging device according to the above-described embodiment may be stored in a computer-readable storage medium (such as a flexible disc, a hard disk, an optical disk, a magneto-optical disk, a CD-ROM, a CD-R, a magnetic tape, a nonvolatile memory card, ROM, EEPROM, or Blu-ray Disc) as a program to be executed by a computer. A still another embodiment may be related to a program for executing by a computer the aforementioned method using the imaging device.

Embodiments

First Embodiment

In a first embodiment, an imaging device (OCT device) using optical coherence tomography to which the present invention is applied will be described with reference to FIGS. 1A and 1B.

As shown in FIG. 1A, an OCT device 100 according to the embodiment constitutes a Michelson type interferometer as a whole. Light emitted from a light source is first split into measuring lights and reference lights. In addition, the measuring lights are provided in a plurality of measuring light paths. The OCT device 100 includes an OCT system that takes a tomographic image of an examination object using a plurality of combined lights in which returning lights of the plurality of measuring lights and the reference lights that have passed through reference light paths are combined and caused to optically interfere with each other. A Mach-Zehnder type interferometer may also be used as an interferometer. If the Mach-Zehnder type interferometer is used, compared to the Michelson type interferometer, a tomographic image obtained when the ratio between the measuring lights and the reference lights is small can have high contrast.

In the specification, the aforementioned tomographic image is also called an "optical coherence tomographic image."

More specifically, in the figure, exiting light 104, which is light that has exited from the light source 101, is guided to a single-mode fiber 110 and is caused to be incident upon an optical coupler 156. At the optical coupler 156, the exiting light 104 is split into exiting lights 104-1 to 104-3 provided in three light paths, that is, a first light path, a second light path, and a third light path.

The exiting lights 104-1 to 104-3 provided in the three light paths pass through polarization controllers 153-1, and are split into reference lights 105-1 to 105-3 and into measuring lights 106-1 to 106-3 through the optical couplers 131-1 to 131-3.

The measuring lights 106-1 to 106-3 split in this way and provided in the three light paths are returned by becoming returning lights 108-1 to 108-3 formed by reflecting or scattering the measuring lights 160-1 to 106-3 by, for example, a retina 127 of an examination eye 107 serving as an observation object. Then, by the optical couplers 131-1 to 131-3, the returning lights 108-1 to 108-3 are combined with the reference lights 105-1 to 105-3 that have passed through the reference light paths and become combined lights 142-1 to 142-3. After the combined lights 142-1 to 142-3 have been formed, they are dispersed for respective wavelengths by the transmission diffraction grating 141. The dispersed lights are incident upon the line sensor 139. The line sensor 139 converts the intensity of light into voltage for each position (wavelength). Using each signal thereof, a tomographic image of the examination eye 107 is formed.

However, the unit for branching a light path into a plurality of light paths is not limited to thereto. Optical couplers 156 for splitting light into reference lights and measuring lights may be disposed at a coupler examination object side and at a coupler reference mirror side, respectively, so that the light is branched into three measuring lights and three reference lights by the couplers. Alternatively, reference light may be provided with only one light path without disposing an optical coupler 156 at the reference mirror side.

Next, the vicinity of the light source 101 will be described. The light source 101 is a super luminescent diode (SLD) which is a typical low-coherent light source. The wavelength thereof is 840 nm, and the bandwidth thereof is 50 nm. Here, the bandwidth is an important parameter because it affects the resolution in an optical axis direction of a tomographic image to be obtained. Although the SLD has been selected as the light source, anything else that can emit low-coherent light, such as an amplified spontaneous emission (ASE) light source, may be used. Considering that an eye is measured, near-infrared light is suitable as the wavelength. In addition, the wavelength affects the resolution in the lateral direction of the tomographic image that is obtained, so that it is desirable for the wavelength to be as short as possible. Here, the wavelength is 840 nm. Depending upon a measuring portion of an observation object, other wavelengths may be selected.

Next, the light paths of the reference lights 105 will be described. The reference lights 105-1 to 105-3 split by the optical couplers 131-1 to 131-3 and provided in the three light paths pass through the polarization controllers 153-2 and fiber length varying units 155-1 to 155-3, become substantially parallel lights at a lens 135-1, and exit from the lens 135-1. Next, the reference lights 105-1 to 105-3 pass through a dispersion compensation glass 115, and are focused on a mirror 114 by a lens 135-2. Next, the reference lights 105-1 to 105-3 change directions at the mirror 114, and travel again towards the optical couplers 131-1 to 131-3. Then, the reference lights 105-1 to 105-3 pass through the optical couplers 131-1 to 131-3, and are guided to the line sensor 139. Here, the dispersion compensation glass 115 compensates for dispersion of the measuring lights 106 reciprocating between the examination eye 107 and the scanning optical system. Here, a typical value as the average eyeball diameter of the Japanese is L=23 mm. Reference numeral 117 denotes an electric stage. The electric stage 117 can be moved in the direction of a double-headed arrow in the figure, and can adjust and control the light path length of the reference lights 105. The electric stage 117 can be controlled by a personal computer 125. Here, although the same mirror 114, the same electric stage 117, and the same dispersion compensation glass 115 are used for the three light paths, they may be independently provided. In such a case, the position of the lens 135 and the position of the mirror 114 are controlled by different electric stages 117 so that the light paths of the reference lights 105-1, 105-2, and 105-3 can be changed.

The fiber length varying units 155-1 to 155-3 are set for the purpose of performing fine adjustments of the lengths of the respective fibers. In accordance with measuring portions of the measuring lights 106-1 to 106-3, the fiber length varying units 155-1 to 155-3 can adjust the light paths of the reference lights 105-1 to 105-3, and can be controlled from the personal computer 125.

Next, the light paths of the measuring lights 106 will be described.

The measuring lights 106-1 to 106-3 split by the optical couplers 131-1 to 131-3 pass through polarization controllers 153-4, become substantially parallel lights at a lens 120-3, exit from the lens 120-3, and are incident upon a mirror of an XY scanner 119 constituting the scanning optical system. Here, for the sake of simplicity, the XY scanner 119 is represented as one mirror. However, the XY scanner 119 actually includes two mirrors, an X scanning mirror and a Y scanning mirror that are disposed close to each other, and performs raster scanning on the retina 127 in a direction perpendicular to the optical axis. A lens 120-1, the lens 120-3, etc. are adjusted so that the center of each of the measuring lights 106-1 to 106-3 is substantially aligned with the rotational center of the mirror of the XY scanner 119.

The lens 120-1 and a lens 120-2 are optical systems for scanning the retina 127 with the measuring lights 106-1 and 106-2, and are used for scanning the retina 127 with the measuring lights with the vicinity of a cornea 126 serving as a pivot. The measuring lights 106-1 to 106-3 are focused on any positions of the retina.

With these any positions serving as centers, the XY scanner 119 is driven to obtain respective scan images. Reference numeral 117-2 denotes an electric stage. The electric stage 117-2 can be moved in the direction of an arrow, and can adjust and control the position of the accompanying lens 120-2. By adjusting the position of the lens 120-2, the measuring lights 106 is focused on a predetermined layer of the retina 127 of the examination eye 107, and the retina 127 can be observed. In addition, abnormal refraction at the examination eye 107 can be dealt with. If the measuring lights 106-1 to 106-3 are incident upon the examination eye 107, the measuring lights 106-1 to 106-3 become the returning lights 108-1 to 108-3 by being reflected or scattered by the retina 127. The returning lights 108-1 to 108-3 pass through the optical couplers 131-1 to 131-3, and are guided to the line sensor 139. Here, the electric stage 117-2 can be controlled by the personal computer 125.

Although, in the embodiment, component parts represented by reference numerals 118-1 to 118-3 are formed so as to be disposed flush with each other (that is, in an XZ plane), the present invention is not limited thereto. They may be disposed in directions perpendicular to the sheet plane of the figure (y direction) or so as to have components of both directions.

By virtue of the above-described structure, three beams can be used for scanning at the same time.

Next, the structure of a measuring system in the OCT device according to the embodiment will be described. The reference lights 105-1 to 105-3 and the returning lights 108-1 to 108-3 formed by reflection or scattering at the retina 127 and traveling through the first and second light paths are combined with each other by the optical couplers 131-1 to 131-3. Then, the combined lights 142 exit from the fiber ends and become substantially parallel lights at the lens 135. The substantially parallel lights illuminate the transmission diffraction grating 141 constituting the detecting section, and are dispersed for the respective wavelengths. The dispersed lights are focused on the imaging lens 143, and the line sensor converts the intensity of the light into a voltage for each position (wavelength). Three interference fringes at spectrum areas on a wavelength axis are observed on the line sensor 139.

Obtaining of a tomographic image using the OCT device will hereunder be described.

Here, obtaining of a tomographic image of the retina 127 (plane parallel to the optical axis) will be described with reference to FIGS. 2A to 2D.

Figure 2A:
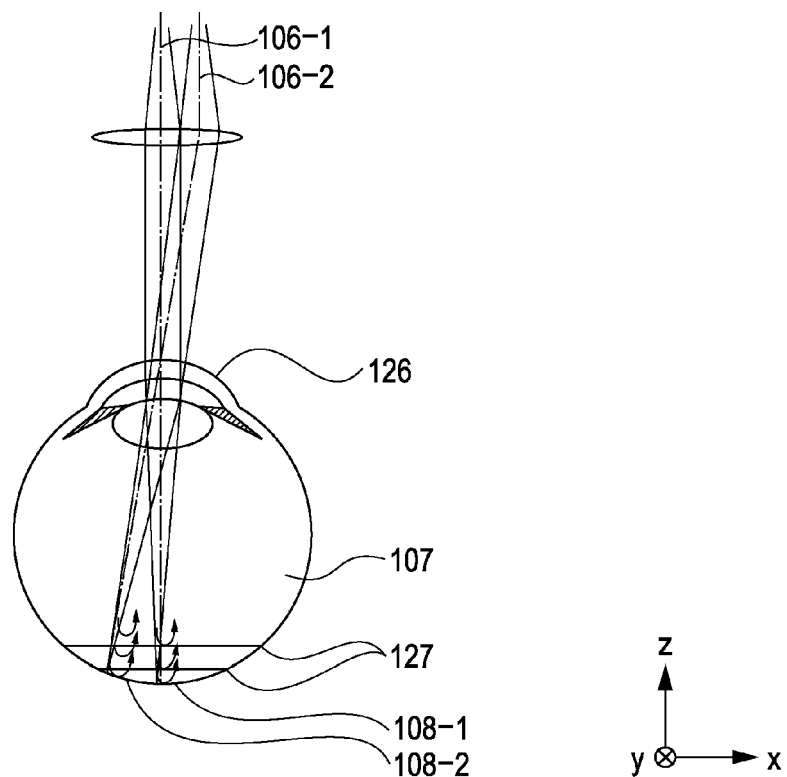
FIGS. 2A to 2D are schematic views illustrating obtainment of a tomographic image of the OCT device in the first embodiment.

FIG. 2A shows a state in which the examination object 107 is observed with the OCT device 100. However, the measuring light 106-3 is not shown.

Since structural members that are the same as or that correspond to those shown in FIG. 1A are given the same reference numerals, the same or corresponding structural members will be not be described below.

As shown in FIG. 2A, the measuring lights 106-1 to 106-3 pass through the cornea 126. When the measuring lights 106-1 to 106-3 are incident upon the retina 127, they are reflected or scattered at various positions and become the returning lights 108-1 to 108-3. With a delay in time at each of the positions, each of the returning lights 108-1 to 108-3 reaches the line sensor 139. In FIG. 2A, for the sake of simplicity, the returning lights 108-1 to 108-3 are shown outside the axis. However, the returning lights 108-1 to 108-3 are actually returning lights traveling along the light paths of the measuring lights 106-1 to 106-3 in the opposite direction. Here, since the bandwidth of the light source 101 is wide and a space coherence length is short, interference fringes can be detected by the line sensor 139 only when the length of the reference light paths and the length of the measuring light paths are substantially equal to each other. As mentioned above, what the line sensor 139 obtains are the interference fringes at the spectrum areas on the wavelength axis. Next, considering the characteristics of the line sensor 139 and the transmission diffraction grating 141, the interference fringes, which are on-wavelength axis information, are converted into interference fringes at an optical frequency axis for the respective combined lights 142-1 to 142-3. Further, by subjecting the converted interference fringes at the optical frequency axis to inverse Fourier transformation, depth-direction information can be obtained.

Figure 2B:
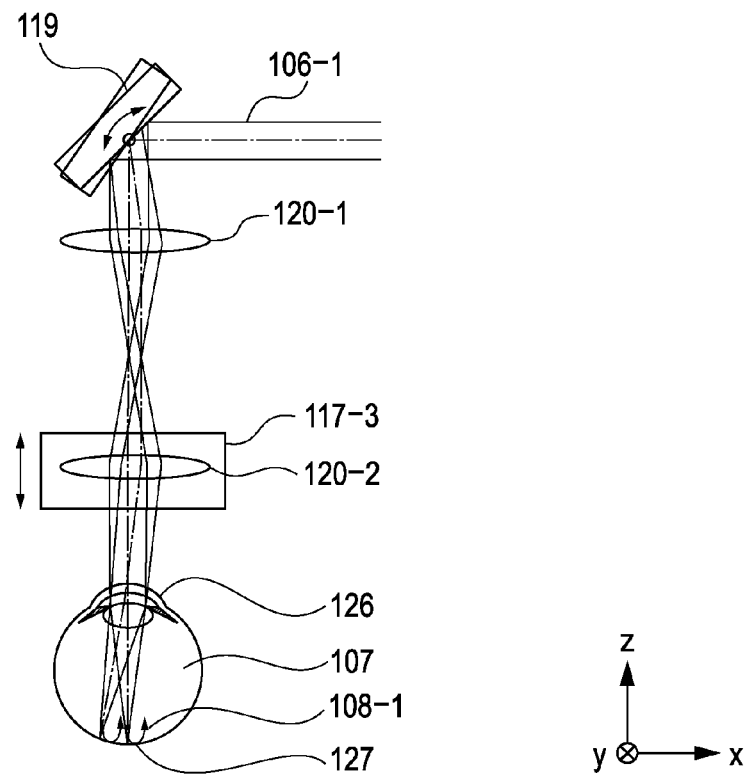

Further, as shown in FIG. 2B (that shows only the measuring light 106-1 among the measuring lights for the sake of simplicity), if the interference fringes are detected while driving an X shaft of the XY scanner 119, the interference fringes for respective X-axis positions are obtained. That is, the depth-direction information for each X-axis position can be obtained.

Figure 2C:
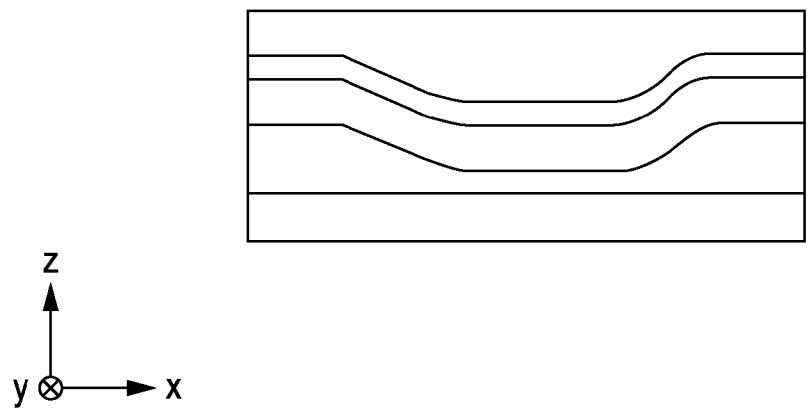

As a result, two-dimensional distribution of the intensity of the returning light 108-1 in the XZ plane is obtained, that is, a tomographic image 132 is obtained (see FIG. 2C). As described above, the tomographic image 132 is actually one in which the intensities of the returning lights 108 are arranged in an array. For example, the intensities are shown by fitting them in a gray scale. Here, only the boundary of the obtained tomographic image is enhanced and shown.

Figure 2D:
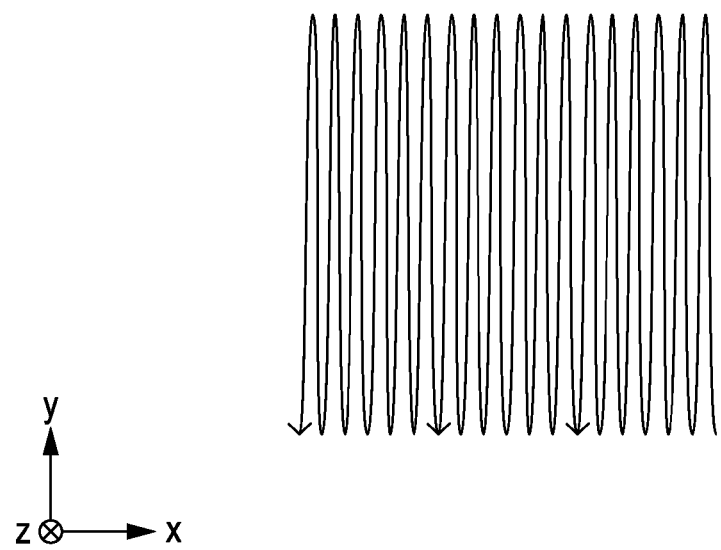

As shown in FIG. 2D, if the XY scanner 119 is controlled, and raster scanning is performed on the retina with the measuring lights 106-1 to 106-3, tomographic images at any two locations on the retina can be continuously obtained at the same time. Here, when the scanning is performed with a main scanning direction of the XY scanner being an X-axis direction and a subscanning direction of the XY scanner being a Y-axis direction, it is consequentially possible to obtain a plurality of tomographic images in the YZ plane.

Next, the spectroscope will be further described in more detail.

FIG. 1B shows a structure in which three combined lights (142-1 to 142-3) are incident upon the OCT device. The fiber ends 160-1 to 160-3 are disposed apart from each other in the y direction, and the combined lights 142-1 to 142-3 exit from the fiber ends 160-1 to 160-3. Here, the orientations of the fiber ends are previously adjusted so that the combined lights exit perpendicularly to a principal surface of the lens, that is, so that telecentricity is achieved. Here, the term "y direction" refers to a direction that is parallel to the direction in which the transmission diffraction grating 141 (serving as a dispersing unit) disperses light. The combined lights that have exited are incident upon the lens 135. In the specification, the lens 135 is also called a "dispersion-side illuminating section." The three combined lights become substantially parallel lights at the lens 135, and are incident upon the transmission diffraction grating 141. The transmission diffraction grating 141 is disposed near a pupil of an optical system (or a substantially conjugate position with respect to a single dispersing unit). It is desirable that a plurality of combined lights be used for illumination so as to intersect at the single dispersing unit. Here, in order to reduce light quantity loss, it is necessary to provide a stop at the surface of the transmission diffraction grating. The transmission diffraction grating 141 is disposed so as to be inclined with respect to the principal surface of the lens 135. Here, it is desirable that the dispersion-side illuminating section 135 perform illumination with the plurality of combined lights at an incident angle with respect to the single dispersing unit. Therefore, light beams at the surface of the transmission diffraction grating 141 (illumination areas of the plurality of combined lights) are elliptical. Consequently, it is necessary for the stop provided at the surface of the transmission diffraction grating 141 to be elliptical. That is, it is desirable that a stop unit having a shape based on the illumination areas of the plurality of combined lights used for illuminating the dispersing unit be provided. The combined lights diffracted by the transmission diffraction grating are incident upon the lens 143 (is also called the "detection-side illuminating unit"). At this time, it is desirable that the detection-side illuminating unit 143 perform illumination on the illumination areas of a plurality of lights at the sensor 139 so that the illumination areas do not overlap each other. Here, the plurality of lights are lights after the plurality of combined lights have passed through the dispersing unit, and correspond to the plurality of combined lights.

The diffracted combined lights in FIG. 1B are light beams only having a center wavelength. For diffracted combined lights having other wavelengths, for the sake of simplicity, only the chief rays are shown. Since the optical axis direction is a z direction, the coordinates are rotated by the diffraction. The diffracted combined lights incident upon the lens 143 are focused on the line sensor 139, and the interference fringes 161-1 to 161-3 in the y direction are observed. That is, the spectroscope is formed so that images at the fiber ends 160-1 to 160-3 become the interference fringes 161-1 to 161-3 on the line sensor 139.

Figure 3A:
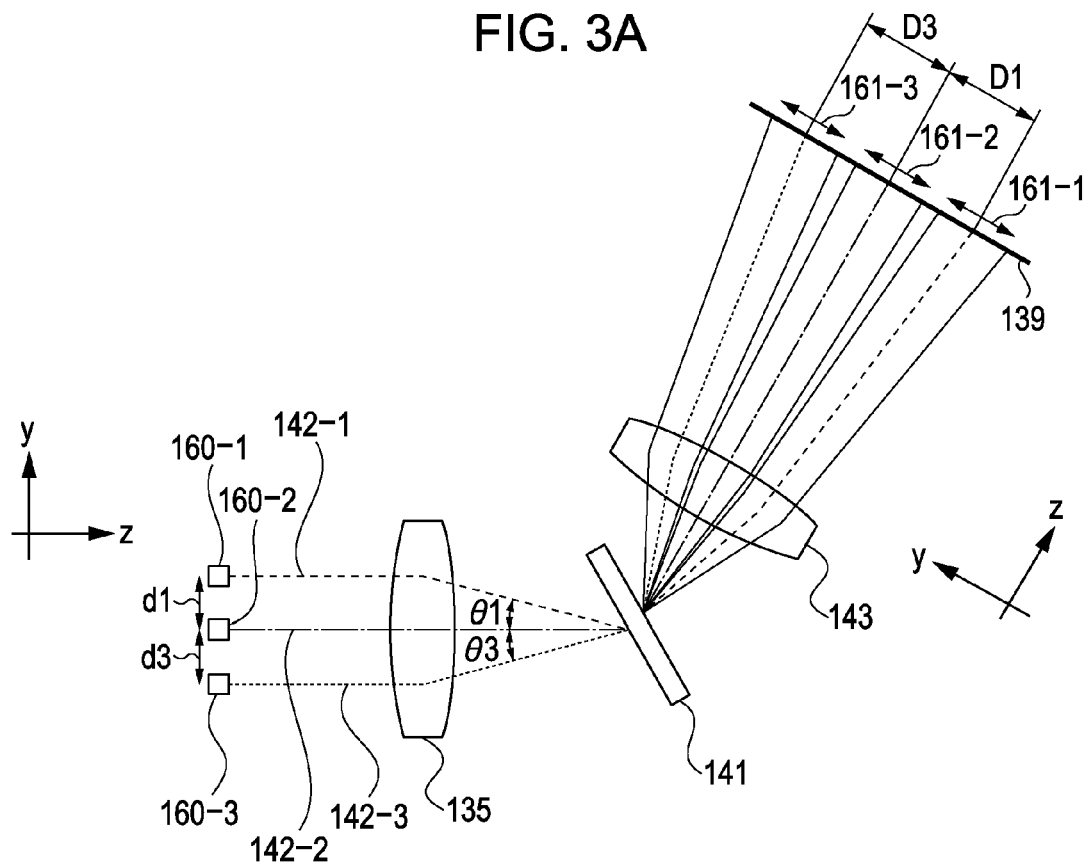
FIGS. 3A and 3B are schematic views illustrating the relationship between the positions of respective members in the structure of a spectroscope in the first embodiment.

FIG. 3A shows the positional relationships in the embodiment. In FIG. 3A, for the sake of simplicity, only the principal rays are shown. If the distance between the fiber end 160-1 and the fiber end 160-2 and the distance between the fiber end 160-3 and the fiber end 160-2 are d1 and d3, respectively; the distances between focus positions of a center wavelength of 840 nm in the line sensor 139 are D1 and D3, respectively; the focal length of the lens 135 is f1, and the inclinations of the rays of the combined lights 142-1 and 142-3 with respect to the optical axis after they have exited from the lens 135 are θ1 and θ3, respectively, the following Expressions (1-1) and (1-3) are established:

$$d1 = f1 \times \tan\theta1 \quad (1\text{-}1)$$

$$d3 = f1 \times \tan\theta3 \quad (1\text{-}2)$$

where d3 and θ3 are negative values.

Figure 3B:
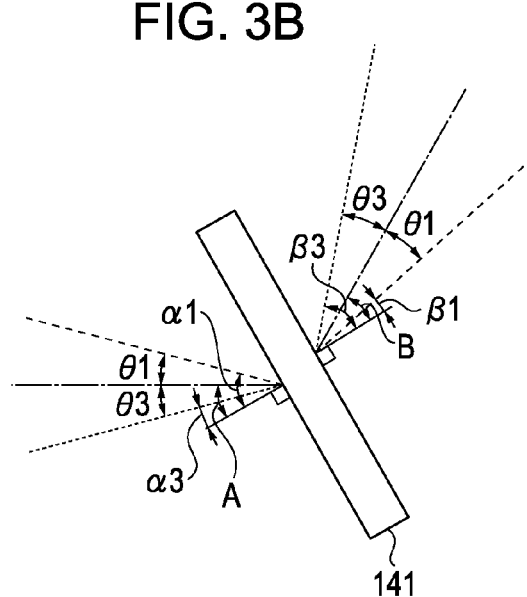

FIG. 3B shows the incident angles with respect to the transmission diffraction grating. If a line that is normal to the transmission diffraction grating is considered as a reference for θ1 and θ3, the incident angles of the combined lights 142-1 and 142-3 with respect to the line that is normal to the transmission diffraction grating are α1 and α3, respectively, and if the incident angle of the combined light 142-2 with respect to the line that is normal to the transmission diffraction grating is A, the following Expressions (2-1) and (2-2) are established:

$$\alpha1 = \theta1 + A \quad (2\text{-}1)$$

$$\alpha3 = \theta3 + A \quad (2\text{-}2)$$

where the incident angle A is set to an incident angle at which the diffraction efficiency of the transmission diffraction grating 141 becomes a maximum. In the specification, diffraction efficiency is also called dispersion efficiency.

If the diffraction angle of an n order light with respect to the incident angle A is B, the following Expression (3) is established:

$$\sin A + \sin B = np\Lambda \quad (3)$$

where p denotes the pitch of the transmission diffraction grating 141. The pitch is related to the width of a pattern that is periodically cut in the transmission diffraction grating 141, and is represented by how many patterns are cut per 1 mm (number of patterns/mm). Λ denotes the wavelength. If n=1 (that is, first order light is used for dispersing the light), and if a diffraction grating is one whose diffraction efficiency becomes a maximum when A=B, the relationship between Δθ and the wavelength width of the light source and the pitch of the diffraction grating is represented by the following Expression (4):

$$A = B = \sin^{-1}(p\Lambda/2) \quad (4)$$

If p=1200 patterns/mm and Λ is 840 nm (center wavelength), A=B=30.26°. The transmission diffraction grating 141 is inclined so that the incident angle of the combined light 142-2 with respect to the line that is normal to the transmission diffraction grating 141 is A=30.26°.

If the diffraction angles of the combined lights 142-1 and 142-3 with respect to the line that is normal to the transmission diffraction grating 141 are β1 and β3, respectively, and the values of the Expression (3) are substituted by these values, the following Expressions (5-1) and (5-2) are established:

$$\sin \alpha 1 + \sin \beta 1 = p\lambda \quad (5-1)$$

$$\sin \alpha 2 + \sin \beta 2 = p\lambda \quad (5-2)$$

If the inclinations of the rays of the combined lights 142-1 and 142-3 with respect to the optical axis of the lens 143 are Θ1 and Θ3, respectively, the following Expressions (6-1) and (6-2) are established:

$$\Theta 1 = \beta 1 - B \quad (6-1)$$

$$\Theta 3 = \beta 3 - B \quad (6-2)$$

Therefore, the focus positions on the line sensor can be represented by the following Expressions (7-1) and (7-2):

$$D1 = f2 \times \tan \Theta 1 \quad (7-1)$$

$$D3 = f2 \times \tan \Theta 3 \quad (7-2)$$

where f2 is the focal length of the lens 143.

Here, if d1 and d3 are 12 mm and −12 mm, respectively, if the focal length of the lens 135 is 100 mm, and if the focal length of the lens 143 is 150 mm, then, D1 and D3 can be both determined. D1 and D3 are −16.81 mm and 19.38 mm, respectively. That is, the combined lights 142-1, 142-2, and 142-3 having a wavelength of 840 nm are focused at the positions of −16.81 mm, 0 mm, and 19.38 mm on the line sensor 139.

Similarly, the focus positions of the combined lights 142-1 to 142-3 having other wavelengths on the line sensor 139 can be obtained by setting A in the Expression (3) to these other wavelengths.

The relationships between the combined lights and the focus positions on a line camera in the first embodiment are shown in Table 1. The focus positions for typical maximum and minimum measuring wavelengths of 865 nm and 815 nm and a typical center wavelength of 840 nm were determined. As can be understood from Table 1, the areas (the numbers of pixels) of the illumination areas of the plurality of lights (that is, the lights after the plurality of combined lights have passed through the dispersing unit) at the sensor 139 differ from each other.

TABLE 1

| COMBINED LIGHT | INCIDENT ANGLE α[°] | WAVELENGTH [nm] | DIFFRACTION ANGLE β[°] | POSITION ON LINE CAMERA [mm] |
|---|---|---|---|---|
| 142-1 | 37.11 | 815 | 22.00 | −21.78 |
|  |  | 840 | 23.87 | −16.81 |
|  |  | 865 | 25.77 | −11.80 |
| 142-2 | 30.26 | 815 | 28.29 | −5.16 |
|  |  | 840 | 30.26 | 0.00 |
|  |  | 865 | 32.28 | 5.27 |
| 142-3 | 23.42 | 815 | 35.49 | 13.71 |
|  |  | 840 | 37.63 | 19.38 |
|  |  | 865 | 39.83 | 25.27 |

Figure 4A:
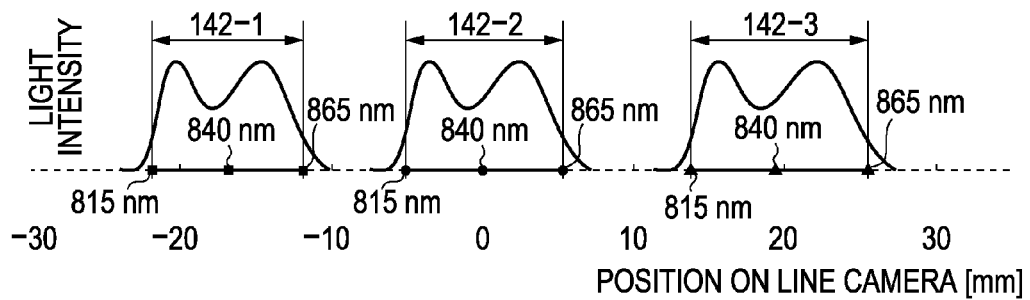
FIGS. 4A to 4C are schematic views illustrating dispersion positions and crosstalk in a line sensor in the first embodiment.
Figure 4B:
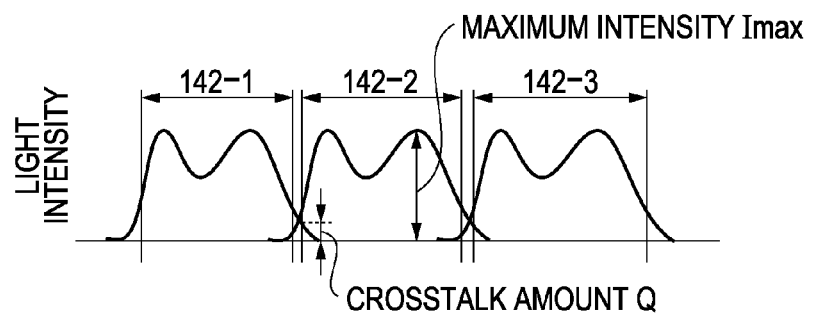

FIG. 4A shows the profiles of the combined lights and the aforementioned relationships. FIG. 4B is a schematic view in which the combined lights are in close contact with each other and are focused on the line sensor 139.

As shown in FIG. 4A, by splitting an area of the line sensor in accordance with the reference numerals 142-1 to 142-3, and by performing, for example, Fourier transformation, it is possible to individually obtain tomographic images of the retina 127 for the measuring lights 106-1 to 106-3. If, as shown in FIG. 4A, focusing is performed when the areas on the line sensor are sufficiently separated from each other so that crosstalk does not occur, no problems occur. However, if, as shown in FIG. 4B, focusing is performed when the areas are in close contact with each other, crosstalk does occur. If crosstalk occurs, the tomographic images of the retina 127 for the measuring lights 106-1 to 106-3 cannot be independently obtained. That is, the tomographic images are obtained when one image overlaps another image. Therefore, it is necessary that the areas be separated from each other on the line sensor so that the images do not overlap each other. If the areas are excessively separated from each other, the pixels of the line sensor are needlessly wastefully used, as a result of which a large number of pixels is required. Therefore, it is also necessary to dispose the areas as close as possible.

Here, if, as shown in FIG. 4B, a maximum value of the light quantity that one of the combining lights contributes to another combining light is defined as a crosstalk amount Q, and a maximum value of the light quantity of the one of the combining lights is Imax, the following Expression (8) needs to be established:

$$Q < I\max \times 10^{-4} \quad (8)$$

By setting the crosstalk amount within the range of the Expression (8), it is essentially possible to obtain good tomographic images without one of the images overlapping another image. If the interference fringes that are focused on the line sensor are brought as close as possible within the range of the Expression (8), the pixels of the line sensors are not wasted.

When an examination object is measured, and a maximum signal level and a noise level are compared with each other, the ratio is approximately $1:10^{-4}$ (40 dB). Therefore, if the crosstalk amount is less than or equal to the range of the Expression (8), the noise level of an image formed by one of the images overlapping another image becomes less than or equal to this noise level, as a result of which the noise at the another image in the one of the images cannot be recognized. In contrast, if the crosstalk amount is greater than or equal to the range of the Expression (8), the noise level of the image formed by one of the images overlapping another image becomes greater than or equal to the noise level, as a result of which the noise at the another image in the one of the images can be recognized. Therefore, an overlapped image is obtained.

That the crosstalk amount Q in the embodiment satisfies the Expression (8) will be indicated below. If a Gauss light source, having a wavelength of 50 nm for a width where the intensity is 1/e² with a center wavelength of 840 nm, is used as the light source 101, a wavelength where the intensity is less than or equal to Imax $10^{-4}$ is less than or equal to 786 nm and greater than or equal to 894 nm. Therefore, if, at the wavelengths of 786 nm and 894 nm, combined light is not included in an adjacent measuring area, the Expression (8) is satisfied. The relationships between the combined lights and the focus positions on the line camera in another embodiment are shown in Table 2. Table 2 shows the focus positions at the wavelengths of 786 nm and 894 nm. The profiles of the combined lights and these positional relationships are added to FIG. 4A and shown in FIG. 4C.

TABLE 2

| COMBINED LIGHT | INCIDENT ANGLE α[°] | WAVELENGTH [nm] | DIFFRACTION ANGLE β[°] | POSITION ON LINE CAMERA [mm] |
|---|---|---|---|---|
| 142-1 | 37.11 | 786 | 19.87 | −27.52 |
|  |  | 840 | 23.87 | −16.81 |
|  |  | 894 | 28.00 | −5.93 |
| 142-2 | 30.26 | 786 | 26.05 | −11.05 |
|  |  | 840 | 30.26 | 0.00 |
|  |  | 894 | 34.67 | 11.55 |
| 142-3 | 23.42 | 786 | 33.07 | 7.36 |
|  |  | 840 | 37.63 | 19.38 |
|  |  | 894 | 42.48 | 32.46 |

Figure 4C:
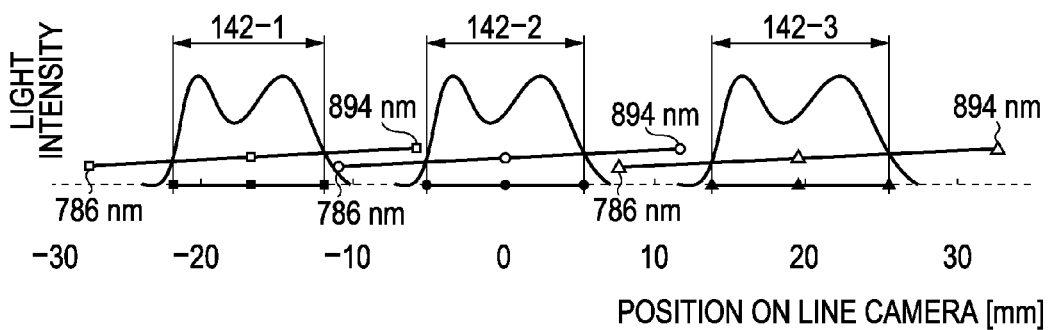

For the sake of simplicity, in FIG. 4C, areas including focus positions at the wavelengths of 786 nm and 894 nm are displaced from areas including focus positions at wavelengths of from 815 nm to 865 nm. The areas including the focus positions of the combined light 142-1 and the combined light 142-3 at the wavelengths of from 786 nm to 894 nm are not included in the areas including the focus positions of the combined light 142-2 at the wavelengths of from 815 nm to 865 nm. In addition, the areas including the focus positions of the combined light 142-2 at the wavelengths of from 786 nm to 894 nm are not included in the areas including the focus positions of the combined lights 142-1 and 142-3 at the wavelengths of from 815 nm to 865 nm. Of the amounts of crosstalk between the combined lights 142-1 to 142-3, if a maximum crosstalk amount Q is estimated, it is a crosstalk amount in which the combined light 142-2 affects the combined light 142-1. It is a crosstalk amount in which light having a wavelength of 781 nm of the combined light affects light having a wavelength of 865 nm of the combined light 142-1. This crosstalk amount Q is $1.45 \times 10^{-5}$. Therefore, since the crosstalk amount is less than Imax$\times 10^{-4}$, the range of the Expression (8) is satisfied.

Therefore, by setting the focal lengths of the lenses 135 and 143, the distances between the fiber ends 160-1 to 160-3, and the pitch in the transmission diffraction grating 141 as mentioned above, it is possible to essentially eliminate overlapping of one image with another when an imaging operation is carried out using OCT, without any crosstalk occurring between the combined lights 142-1 to 142-3 on the line sensor 139. However, the focal lengths of the lenses 135 and 143, the distances between the fiber ends 160-1 to 160-3, and the pitch in the transmission diffraction grating 141 that are set are merely examples in the embodiment among other combinations of focal lengths, distances, and pitches. Accordingly, even if the combination thereof is changed, it is possible for the crosstalk to be within the range of the Expression (8).

Using the Expressions (1) to (7), a focus position D on the line sensor is determined by the following Expression (9):

[Math. 1]

$$D = -f2\tan\left(-\sin^{-1}\left(-\sin\left(\tan^{-1}\left(\frac{d}{f1}\right)+\sin^{-1}\left(\frac{p\Lambda}{2}\right)\right)+p\lambda\right)+\sin^{-1}\left(\frac{p\Lambda}{2}\right)\right)$$

If, in the Expression (9), d=0, the following Expression (10) is established:

[Math. 2]

$$D0 = -f2\tan\left(-\sin^{-1}\left(\frac{p\Lambda}{2}-p\lambda\right)+\sin^{-1}\left(\frac{p\Lambda}{2}\right)\right) \quad (10)$$

In the embodiment, the crosstalk between the combined lights 142-2 and 142-1 is calculated using the Expressions (8) and (9). If the focus position of a wavelength having an intensity of Imax$\times 10^{-4}$ with respect to the intensity of the center wavelength emitted from the fiber ends separated from each other by d, and the distance between the focus positions of the measuring wavelengths at d=0 are greater than or equal to 0, the crosstalk satisfies the Expression (8). As mentioned above, if a measurement is made at the wavelength width where the intensity is 1/e² with respect to the center wavelength, and a Gauss light source is used, the wavelength at which the intensity becomes Imax$\times 10^{-4}$ is a wavelength that has advanced 6/5 times λmax-Λ from the measuring wavelength. In the embodiment, since λmax-Λ is 25 nm, the wavelength is 865 nm+30 nm=895 nm. As can be understood from Tables 1 and 2 and FIG. 4C, the distance between the focus positions of the combined lights 142-3 and 142-2 is less than the distance between the focus positions of the combined lights 142-2 and 142-1. This results from the nature of a diffraction angle. Therefore, the conditions for crosstalk become stricter when d in the Expression (9) is a negative value than when it is a positive value. Considering the aforementioned conditions, satisfying the following Expression (11) results in equivalence to the Expression (8):

[Math. 3]

$$-f2\tan\left(-\sin^{-1}\left(\frac{p\Lambda}{2}-p\lambda_{min}\right)+\sin^{-1}\left(\frac{p\Lambda}{2}\right)\right) > \\ -f2\tan\left(-\sin^{-1}\left(-\sin\left(\tan^{-1}\left(\frac{d_{max}}{f1}\right)+\sin^{-1}\left(\frac{p\Lambda}{2}\right)\right)+p\lambda_{max\ over}\right)+ \\ \sin^{-1}\left(\frac{p\Lambda}{2}\right)\right) \quad (11)$$

However, dmax represents the maximum value among the distances of the fiber ends 160-1 to 160-3, λmin represents a minimum wavelength of the measuring wavelengths, and λmaxover represents a wavelength that has advanced 6/5 times λmax-Λ from the maximum wavelength among the measuring wavelengths. By satisfying this condition, it is possible for the crosstalk between the combined lights 142-1 and 142-2 and that between the combined lights 142-2 and 143-3 to be less than or equal to the range of the Expression (8).

Although, in the foregoing description, crosstalk between first-order lights is considered, crosstalk also occurs between a first-order light and a second-order light. The second-order light is detected at a position opposite to the combined light 142-2 at the combined light 142-3. That is, the second-order light is disposed at a location where the crosstalk between the first-order light of the combined light 142-3 and the second-order light of the combined light 142-1 is closest. The focus position of λmax of the first-order light 142-3 and the focus position of λmin of the second-order light 142-1 are estimated below.

For the former, λ in the Expression (9) is λmax:

[Math. 4]

$$D = -f2\tan\left(-\sin^{-1}\left(-\sin\left(\tan^{-1}\left(\frac{d_{min}}{f1}\right) + \sin^{-1}\left(\frac{p\Lambda}{2}\right)\right) + p\lambda_{max}\right) + \sin^{-1}\left(\frac{p\Lambda}{2}\right)\right) \quad (12)$$

where dmin represents the minimum distance among the distances of the fiber ends 160-1 to 160-3, and is d3 in the embodiment.

For the latter, the Expression (9) is solved for the second-order light, and Expression (13) is established:

[Math. 5]

$$D = -f2\tan\left(-\sin^{-1}\left(-\sin\left(\tan^{-1}\left(\frac{d_{min}}{f1}\right) + \sin^{-1}\left(\frac{p\Lambda}{2}\right)\right) + 2p\lambda_{min\,over}\right) + \sin^{-1}\left(\frac{p\Lambda}{2}\right)\right) \quad (13)$$

where dmax represents the maximum distance among the distances of the fiber ends 160-1 to 160-3, and is d1 in the embodiment. λminover represents a wavelength that is 6/5 times of λmax-Λ below the maximum wavelength among the measuring wavelengths.

Therefore, if the value of the Expression (12) is less than that of the Expression (13), the aforementioned crosstalk does not occur. Therefore, it is necessary to satisfy the following Expression (14):

[Math. 6]

$$-f2\tan\left(-\sin^{-1}\left(-\sin\left(\tan^{-1}\left(\frac{d_{min}}{f1}\right) + \sin^{-1}\left(\frac{p\Lambda}{2}\right)\right) + p\lambda_{max}\right) + \sin^{-1}\left(\frac{p\Lambda}{2}\right)\right) < \quad (14)$$
$$-f2\tan\left(-\sin^{-1}\left(-\sin\left(\tan^{-1}\left(\frac{d_{max}}{f1}\right) + \sin^{-1}\left(\frac{p\Lambda}{2}\right)\right) + 2p\lambda_{min\,over}\right) + \sin^{-1}\left(\frac{p\Lambda}{2}\right)\right)$$

In the embodiment, a right-side solution does not exist, and second-order light is prevented from being generated. The condition thereof is as follows:

$$p\lambda < -1 \text{ or } p\lambda > 1 \quad (15)$$

It is necessary to satisfy the Expression (14) with regard to the conditions that generate second-order light, by, for example, changing the pitch p of the diffraction grating.

The relationship between the focus positions on the area sensor 139 indicated here does not consider the influence of distortion of the optical system. In ordinary optical systems, distortion occurs. Therefore, the focus positions are shifted by a range of a few percent from the positions indicated here. However, the distortion is within a range of a few percent. In addition, even if distortion occurs, the focus positions of all the wavelengths are shifted towards or away from the position of y=0. Therefore, crosstalk having a large effect is not generated. However, if, for example, a rotationally asymmetrical surface or a free-form surface is used in the lens 135 or the lens 143, aspherical distortion may occur. If the aspherical distortion is large, the distances d1 and d2 are made adjustable.

The lens 135 and the lens 143 used here may include a plurality of lenses. Alternatively, they may each be provided with a plurality of mirrors or a mirror having the same focal length. Further, although, in the embodiment, the transmission diffraction grating is used as the dispersing unit, a reflective diffraction grating or an element that can split a wavelength, such as a prism, may also be used.

Second Embodiment

In the first embodiment, the fiber ends 160-1 to 160-3 are disposed in the y direction, and three interference fringes observed in the y direction can be detected by one line sensor. In contrast, in a second embodiment, fiber ends 160-1 to 160-3 are disposed in the x direction, and three interference fringes observed in the x direction are detected by a sensor. Here, the term "x direction" refers to a direction that is perpendicular to a dispersion direction of a transmission diffraction grating 141 serving as a dispersing unit. The embodiment will be described below.

The structure of an OCT device in the second embodiment is the same as that of the OCT device according to the first embodiment shown in FIG. 1A, so that it will not be described below.

Here, a dispersing section will be described in detail.

Figure 5A:
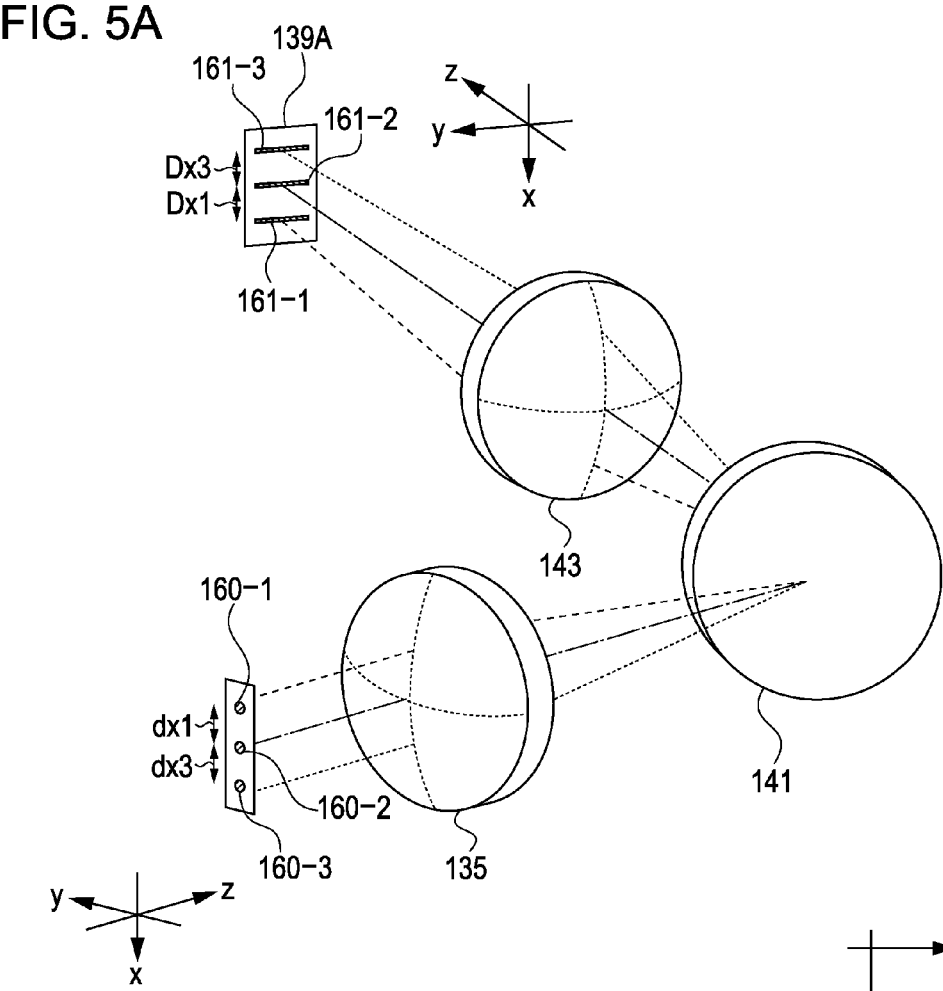
FIGS. 5A and 5B are schematic views illustrating the structure of a spectroscope in the second embodiment.

FIG. 5A shows a structure in which combined lights (142-1 to 142-3) are incident upon the OCT device. Here, for the sake of simplicity, only chief rays having a wavelength of 840 nm are shown. The combined lights 142-1 to 142-3 exit from fiber ends 160-1 to 160-3. Similarly to the first embodiment, the orientations of the fiber ends are previously adjusted so that the combined lights exit perpendicularly to a principal surface of a lens. The combined lights that have exited from the principal surface are incident upon a lens 135. The three combined lights become substantially parallel lights at the lens 135, and are incident upon the transmission diffraction grating 141. As in the first embodiment, in order to reduce light quantity loss, it is necessary for the transmission diffraction grating to be disposed near the pupil of the optical system, for a stop to be disposed at the surface of the transmission diffraction grating 141, and for the stop to be elliptical. The combined lights diffracted at the transmission diffraction grating 141 are incident upon a lens 143. The combined lights incident upon and diffracted by the lens 143 are focused on a line sensor array 139A, and become interference fringes 161-1 to 161-3. That is, a spectroscope is formed so that images at the fiber ends 160-1 to 160-3 become the interference fringes 161-1 to 161-3 on the area sensor array 139A. In the line sensor array 139A, three line sensors are disposed in a row in the x direction, and the interference fringes are formed on the three line sensors. The area sensor array 139A may be an area sensor.

Figure 5B:
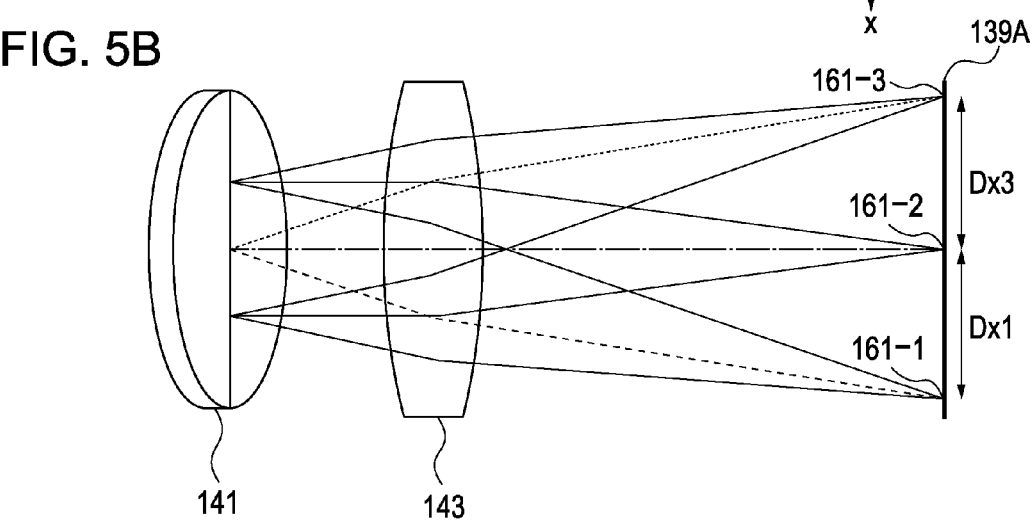

A light path extending from the transmission diffraction grating 141, through the lens 143, and to the line sensor array 139A is shown as cut by an xz plane in FIG. 5B. The light rays that have exited from the transmission diffraction grating 141 pass through the lens 143 and are focused on the area sensor array 139A. Since the transmission diffraction grating 141 is a first-order transmission diffraction grating 141, diffraction does not occur when the light path is cut by the xz plane. Therefore, the interference fringes are observed only in the y direction, and are not observed in the x direction.

Here, dx1 and dx3 are 1 mm and −1 mm, respectively; and, as in the first embodiment, the focal length of the lens 135 is 100 mm, the focal length of the lens 143 is 150 mm, the pitch of the transmission diffraction grating 141 used is p=1200 patterns/mm, and a light source having a center wavelength of 840 nm is used. Since, as mentioned above, diffraction does not occur in the x direction, Dx1 and Dx3 are distances resulting from multiplying the magnification of the optical system to dx1 and dx3, respectively. The magnification is −(150/100)=−1.5. That is, Dx1 and Dx3 are −1.5 mm and 1.5 mm, respectively. The combined lights 142-1, 142-2, and 142-3 are focused at −1.5 mm, 0 mm, and 1.5 mm in the x direction.

Crosstalk between the interference fringes 161-2 and 161-1 and that between the interference fringes 161-2 and 161-3 will be described below. Since diffraction does not occur in the xy plane as mentioned above, the interference fringes are not observed in the x direction. Therefore, the crosstalk between the interference fringes 161-2 and 161-1 and the crosstalk between the interference fringes 161-2 and 161-3 are determined by spot diameters of the interference fringes 161-1 to 161-3. Though depending upon aberrations of the optical system, if the aforementioned optical system is used, the spot diameters on the area sensor array 139A are approximately over 10 um to several tens of um. Considering a spot shape of over 10 um in a width where the intensity is $1/e^2$, the position at which the intensity becomes $10^{-4}$ is a position separated by approximately 100 um. Therefore, the interference fringes that are focused upon the positions of −1.5 mm, 0 mm, and 1.5 mm on the line sensor array 139A are further away than the 100 um where the intensity becomes $10^{-4}$. Therefore, the crosstalks are less than or equal to that obtained by the Expression (8). Consequently, in the embodiment, the condition that satisfies the Expression (8) is as follows:

$$dx \times \beta > 0.1 \text{ mm} \tag{16}$$

Although, in the embodiment, the fiber ends 160-1 to 160-3 are disposed in the x direction, they may be rotated from the x direction to the y direction and disposed. If the rotational angle from the x direction is φ, when x components of the fiber ends are calculated, the relationship becomes the same as that mentioned above. Therefore, similar effects can be obtained if Expression (17) is established:

$$dx \times \cos\phi \times \beta > 0.1 \text{ mm} \tag{17}$$

If the focus positions of the combined lights 161-1 to 161-3 are excessively separated from each other on the line sensor array 139A, spot diameters are increased or distortion occurs due to optical aberrations. This reduces light-receiving efficiency of the line sensor array and reduces image quality.

The optical aberrations are smaller as light passes close to the center of the lens 143, and are larger as the light passes closer to the outer side of the lens 143. If the optical aberrations on the line sensor array 139A are compared, the optical aberrations become larger with greater distance from the center (the focus position of the wavelength of 840 nm of the combined light (161-2). Therefore, the distances Dx1 and Dx3 need to be on the order of the dispersion width on the line sensor array 139A. That is, using Expression (10), it is necessary to satisfy the following relationship or Expression (18):

[Math. 7]

$$dx \times \beta < \frac{\left[-f2\tan\left(-\sin^{-1}\left(\frac{p\Lambda}{2} - p\lambda_{max}\right) + \sin^{-1}\left(\frac{p\Lambda}{2}\right)\right)\right] - \left[-f2\tan\left(-\sin^{-1}\left(\frac{p\Lambda}{2} - p\lambda_{min}\right) + \sin^{-1}\left(\frac{p\Lambda}{2}\right)\right)\right]}{2} \tag{18}$$

If the fiber ends 160-1 to 160-3 are rotated by the rotational angle φ from the x direction to the y direction, the left side becomes dx×cos φ×β:

[Math. 8]

$$dx \times \cos\phi \times \beta < \frac{\left[-f2\tan\left(-\sin^{-1}\left(\frac{p\Lambda}{2} - p\lambda_{max}\right) + \sin^{-1}\left(\frac{p\Lambda}{2}\right)\right)\right] - \left[-f2\tan\left(-\sin^{-1}\left(\frac{p\Lambda}{2} - p\lambda_{min}\right) + \sin^{-1}\left(\frac{p\Lambda}{2}\right)\right)\right]}{2} \tag{19}$$

By satisfying the Expressions (16) and (18) and the Expressions (17) and (19), it is possible to minimize optical aberrations while reducing crosstalk to substantially zero.

Third Embodiment

In the first and second embodiments, three separate light paths are provided, the measuring lights 106-1 to 106-3 are focused on any positions on the retina, and the three interference fringes are detected with one line sensor. In contrast, in a third embodiment, nine separate light paths are provided, measuring lights are focused on any positions on the retina, and nine interference fringes are detected with one line sensor including a plurality of lines.

The structure of an interferometer in the third embodiment is such that three light paths shown in FIG. 1A according to the first embodiment are replaced by nine light paths. The other basic structural elements are the same, and will not be described below.

Here, a dispersing section will be described in detail.

FIG. 6 shows a structure in which nine combined lights (142-1 to 142-9) are incident upon an OCT device. Here, for the sake of simplicity, light rays are not shown. When light paths are cut by a yz plane, the structure in FIG. 6 is exactly the same as that in FIG. 1B. The light paths extending from a transmission diffraction grating 141, through a lens 143, and to a line sensor array 139A have structures that are the same as that in FIG. 5B when cut by an xz plane. The combined lights 142-1 to 142-9 exit from fiber ends 160-1 to 160-9. Similarly to the first and embodiments, the orientations of the fiber ends are previously adjusted so that the combined lights exit perpendicularly to a principal surface of a lens. The combined lights that have exited from the principal surface are incident upon a lens 135. The nine combined lights become substantially parallel lights at the lens 135, and are incident upon a transmission diffraction grating 141. As in the first and second embodiments, in order to reduce light quantity loss, it is necessary for the transmission diffraction grating 141 to be disposed near the pupil of the optical system, for a stop to be disposed at the surface of the transmission diffraction grating 141, and for the stop to be elliptical. The combined lights diffracted at the transmission diffraction grating 141 are incident upon a lens 143. The combined lights incident upon and diffracted by the lens 143 are focused on a line sensor array 139A, and become interference fringes

161-1 to 161-9. That is, a spectroscope is formed so that images at the fiber ends 160-1 to 160-9 become the interference fringes 161-1 to 161-9 on the area sensor array 139A. In the line sensor array 139A, three line sensors are disposed in a row in the x direction, and three interference fringes each are formed on the three line sensors (that is, a total of nine interference fringes are formed). The area sensor array 139A may be an area sensor.

Figure 7A:
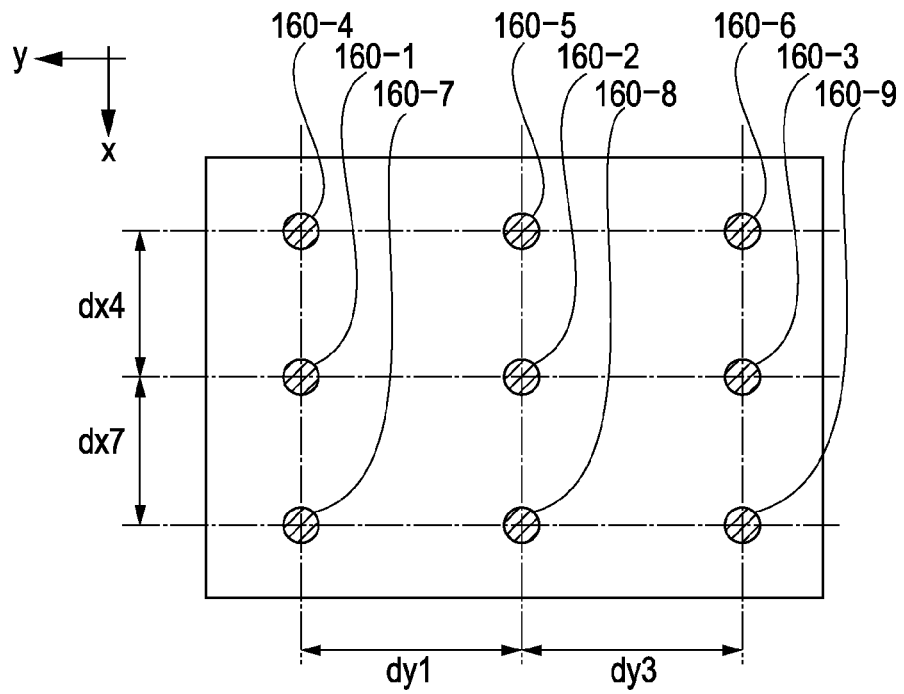
FIGS. 7A and 7B are schematic views illustrating the relationship between the positions of respective members in the structure of the spectroscope in the third embodiment.

FIG. 7A shows the structure of the fiber ends 160-1 to 160-9. The fiber ends 160-1 to 160-9 are disposed as shown in FIG. 7A so as to be separated by distances dy1 and dy3 in the y direction and by distances dx4 and dx7 in the x direction.

Figure 7B:
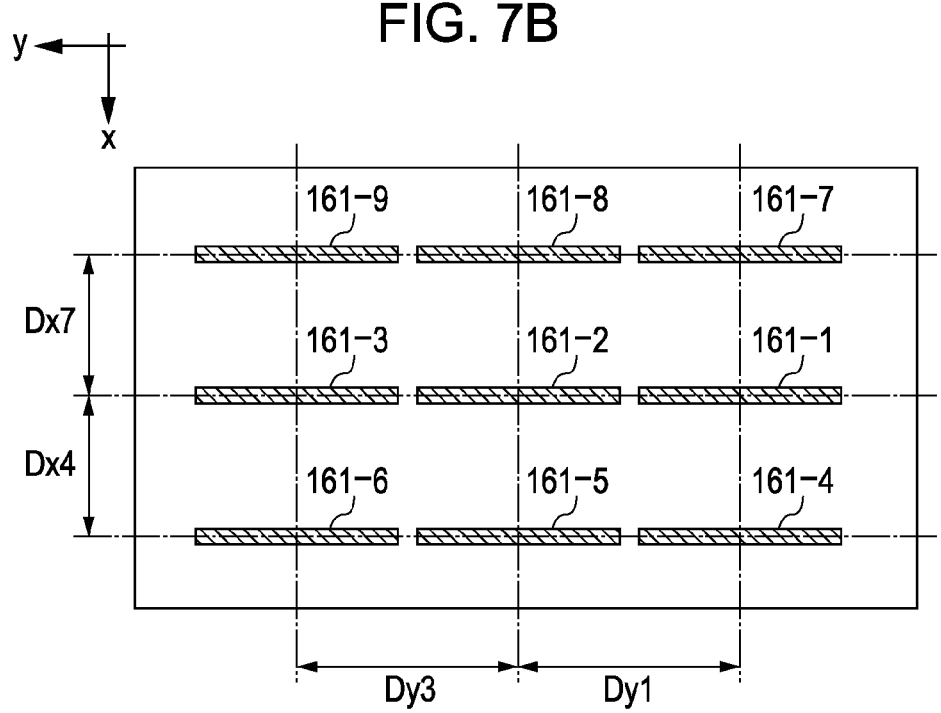

FIG. 7B shows the interference fringes focused on the line sensor array 139A. Black portions correspond to the interference fringes 161-1 to 161-9. The fiber ends 160-1 to 160-9 in FIG. 7A are used for focusing at the interference fringes 161-1 to 161-9. The interference fringes 161-1 to 161-9 are disposed in a row so as to be separated by distances Dy1 and Dy3 in the y direction and by distances Dx4 and Dx7 in the x direction.

When, as mentioned above, the light paths according to the embodiment are cut in the yz plane, the structure is exactly the same as that in FIG. 1B in the first embodiment. Light paths extending from the transmission diffraction grating 141, through the lens 143, and to the line sensor array 139A are the same as those in FIG. 5B when cut by the xz plane.

Here, if, as in the first embodiment, dy1 and dy2 are 12 mm and −12 mm, respectively, the focal length of the lens 135 is 100 mm, the focal length of the lens 143 is 150 mm, the pitch of the transmission diffraction grating used is p=1200 patterns/mm, and a light source having a center wavelength of 840 nm is used, then, Dy1 and Dy3 become −16.81 and 19.38 mm, respectively, which are the same as D1 and D3 in the first embodiment. That is, lights having a wavelength of 840 nm of the combined lights 142-1, 142-4, and 142-7, the combined lights 142-2, 142-5, and 142-8, and the combined lights 142-3, 142-6, and 142-9 are focused upon the positions of −16.89 mm, 0 mm, and 19.38 mm on the line sensor array 139A in the y direction. In the same way, for the focus positions on the line sensor array 139A of the wavelengths of the combined lights 142-1 to 142-9, A in Expression (3) can be obtained for the wavelengths. These are the same as those in the first embodiment. The focus positions of the maximum wavelength of 865 nm, the minimum wavelength of 815 nm, and the center wavelength of 840 nm are shown in Table 3. Even the relationships between the crosstalks are the same as those in the first embodiment, so that they satisfy Expression (8).

TABLE 3

| COMBINED LIGHT | WAVE-LENGTH [nm] | POSITION ON LINE CAMERA (y DIRECTION) [mm] |
|---|---|---|
| 142-1, 4, 7 | 815 | −21.78 |
|  | 840 | −16.81 |
|  | 865 | −11.80 |
| 142-1, 5, 8 | 815 | −5.16 |
|  | 840 | 0.00 |
|  | 865 | 5.27 |
| 142-3, 6, 9 | 815 | 13.71 |
|  | 840 | 19.38 |
|  | 865 | 25.27 |

If, as in the second embodiment, dx4 and dx7 are 1 mm and −1 mm, respectively, Dx4 and Dx7 become 1.5 mm and −1.5 mm, respectively. Therefore, the combined lights 142-1, 142-2, and 142-3, the combined lights 142-4, 142-5, and 142-6, and the combined lights 142-7, 142-8, and 142-9 are focused at the positions of 0 mm, 1.5 mm, and −1.5 mm in the x direction. Since the focus positions are sufficiently separated from each other compared to the spot diameters, and the relationship is the same as that in the second embodiment, the crosstalks satisfy the Expression (8).

In the embodiment, the distances between the fiber ends 160-1 to 160-9 in the x direction are less than the distances between the fiber ends 160-1 to 160-9 in the y direction. This is related to a diffraction direction of the transmission diffraction grating 141. In the embodiment, since the transmission diffraction grating 141 that diffracts light in the y direction and that does not diffract light in the x direction is used, interference fringes are observed in the y direction on the area sensor array 139A. Therefore, as mentioned in the first embodiment, if crosstalk is considered, it is necessary for the fiber ends to be separated from each other by a certain distance. In contrast, in the x direction, as mentioned in the second embodiment, since interference fringes are not observed, is determined by the spot diameters, thereby making it unnecessary to separate the fiber ends by distances that are as large as those in the y direction. Since the spot diameters are approximately over 10 um to several tens of um, if the distance in the x direction on the area sensor array 139A is 1.5 mm, crosstalk is satisfactorily prevented from occurring, and the Expression (8) is satisfied even in the x direction. Therefore, in the embodiment, the distances between the fiber ends 160-1 to 160-9 in the x direction are smaller than those in the y direction, thereby reducing the size of the device.

Fourth Embodiment

A fourth embodiment differs from the first embodiment in that a mechanism that can adjust at all times the distances between fiber ends, that is, d1 and d3 in FIG. 3A is provided. This makes it possible to correct any displacement of interference light beams on a line sensor by changing with time, for example, an optical arrangement including the fiber ends. Therefore, even if changes occur with time, crosstalk does not occur. Component parts that are similar to those in the first embodiment will not be described.

A specific fiber-end adjusting mechanism will be described with reference to FIGS. 8A and 8B.

Reference numeral 1000 denotes a fiber-end unit section.

Reference numerals 1003-1 to 1003-3 denote fibers connected to splitting sections of optical couplers 131-1 to 131-3. The fibers 1003-1 to 1003-3 are fibers whose center members are formed of, for example, quartz. A fiber-end-160-1 side, a fiber-end-160-2 side, and a fiber-end-160-3 side of the fibers 1003-1 to 1003-3 are polished and secured to holding sections 1001-1 to 1001-3, respectively. Further, the holding sections 1001-1 to 1001-3 are adhered and secured to fiber base sections 1002-1 to 1002-3 including guide sections for making adjustments.

The center fiber base section 1002-2 is secured to a base 1010 with, for example, a screw (not shown). When the base 1010 is adjusted by moving optical positions (x, y) and a focus position (z) with respect to the lens 135 shown in FIG. 1B, the base 1010 is at an optimal position with respect to the center fiber end 160-2.

Figure 8A:
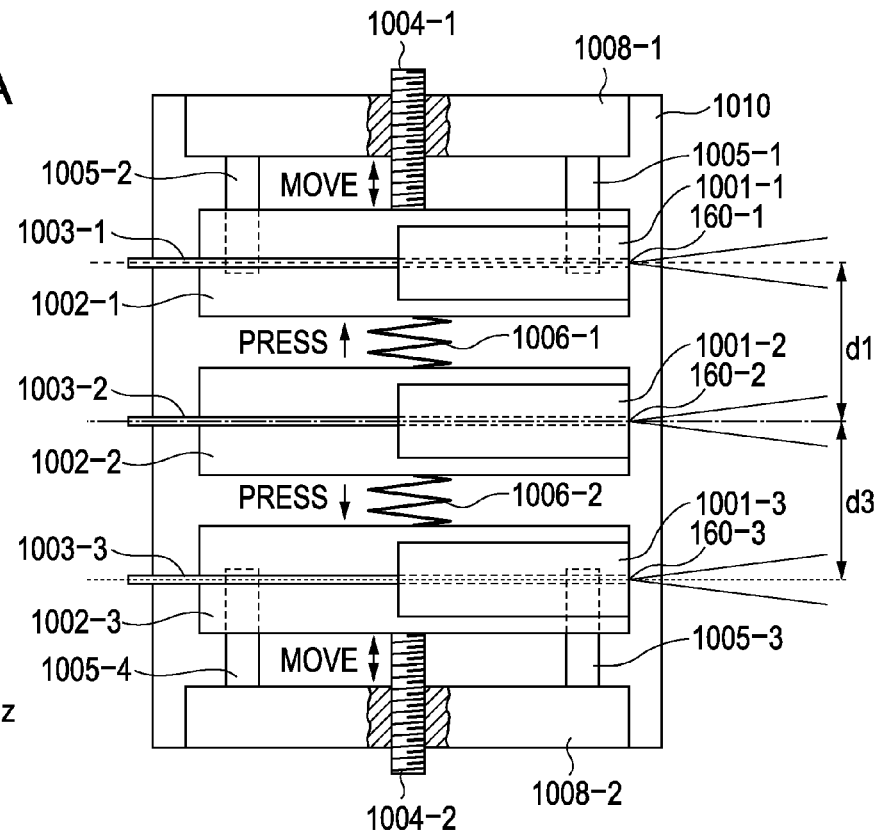
FIGS. 8A and 8B illustrate an adjusting mechanism of fiber ends in a fourth embodiment.

The upper fiber section 1002-1 and the lower fiber section 1002-3 in FIG. 8A are movable with respect to the center fiber base section 1002-2 relative to a fiber distance direction (y direction). Taking the upper fiber base section 1002-1 is taken as an example, the guide section, where pins 1005-1 and 1005-2 are inserted in the fiber base section 1002-1, is provided with respect to the pins 1005-1 and 1005-2 to which a y guide member 1008-1 is secured, and is movably held in the y direction. In addition, a spring 1006-1 is provided between the fiber base sections 1002-1 and 1002-2. By this, the fiber base section 1002-1 is pressed in the direction of an arrow (y direction or pressing direction). The y guide member 1008-1 is provided with a threaded hole, and is provided with an adjusting screw 1004-1. The adjusting screw 1004-1 contacts the fiber base section 1002-1, and is positioned in the y direction of the fiber base section 1002-1. By rotating the adjusting screw 1004-1, the distance between the fiber base sections 1002-1 and 1002-2 can be changed in the direction of an arrow (movement direction), as a result of which d1, which is the distance between the fiber ends 160-1 and 160-2, can be adjusted. By also providing a similar structure to the fiber base section 1002-3, d3 can be adjusted. By such a mechanism, when assembling a device, d1 and d3 can be initially adjusted.

When adjusting d1 and d3 in the figure, the following procedure is carried out.

Figure 9A:
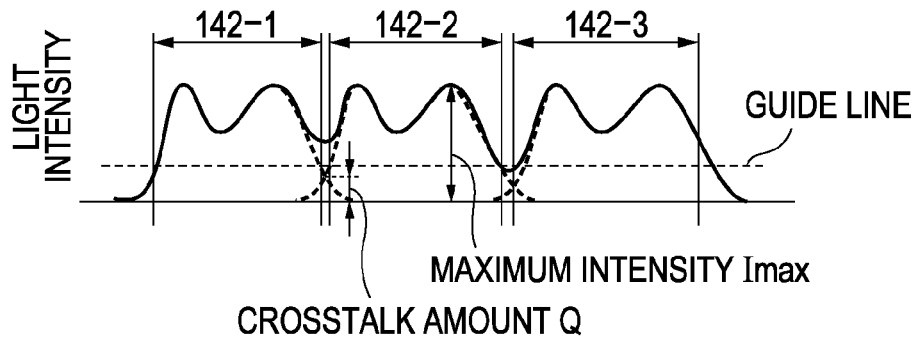
FIGS. 9A to 9C illustrate intensity distributions of interference lights in the fourth embodiment.
Figure 9B:
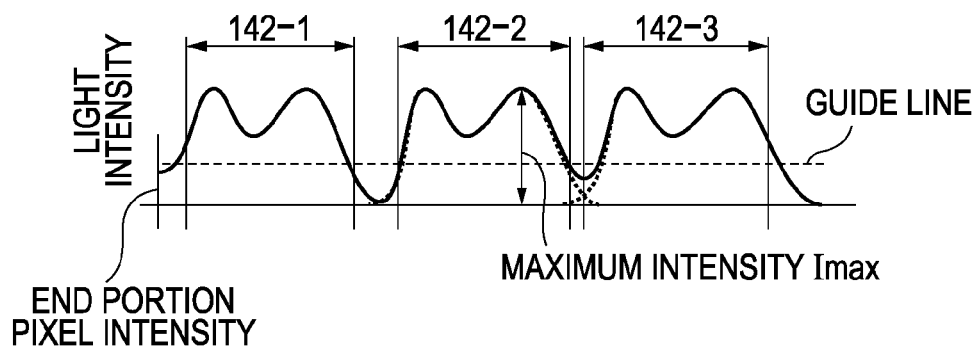
Figure 9C:
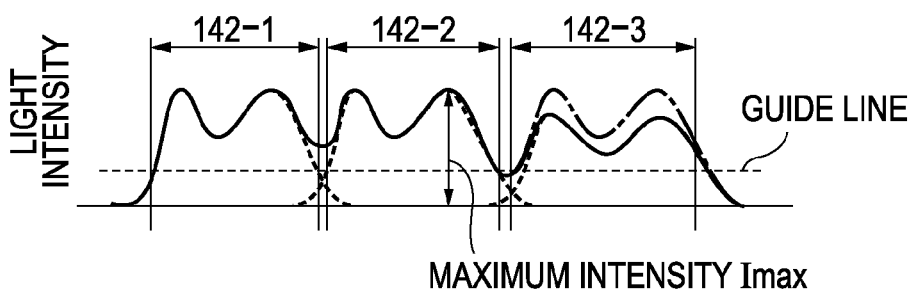

Using the computer 125 shown in FIG. 1A, images that indicate the distributions of the intensities of interference lights obtained at the line sensor 139 are output. The output images are displayed on a monitor (not shown). Exemplary output images are shown in FIGS. 9A to 9C. The distributions of the intensities of the interference lights that are displayed result from adding the intensities of the interference lights 142-1 to 142-3. The intensity distributions resulting from adding the intensities of the interference lights 142-1 to 142-3 are indicated by solid lines, and the distribution of the intensity of each single interference light is indicated by a dotted line. Along with the intensity distributions, guide lines of the intensities of crosstalk sections determined from threshold values of crosstalk amounts Q are also shown. Each guide line indicates a value of $I_{max} \times 10^{-4} \times 2$, that is, the sum of the threshold values $I_{max} \times 10^{-4}$, which determine the crosstalk amount by the Expression (8) for the interference lights 142-1 and 142-2.

FIG. 9A shows an example in which d1 is small due to changes with time. If the sum of the intensities of the interference lights 142-1 and 142-2 at a pixel where a maximum crosstalk occurs exceeds the guide line, the adjusting screw 1004-1 is rotated (towards the left for a right-handed screw) to increase d1, thereby moving the interference lights 142-1 and 142-2 away from each other on the line sensor 139. In addition, they are displayed below the guide line.

In contrast, if, as shown in FIG. 9B, d1 is increased with changes with time, the interference light 142-1 extends beyond the line sensor 139. In this case, the adjusting screw 1004-1 is rotated (towards the right for a right-handed screw) to reduce d1, thereby moving the interference lights 142-1 and 142-2 close to each other on the line sensor 139. The adjusting screw 1004-1 is rotated until the entire interference light 142-1 can be taken in by the line sensor 139.

The case in which, as in the first embodiment, a maximum crosstalk amount is produced due to the crosstalk between the interference lights 142-2 and 142-1, and the intensity of the interference light 142-2 is high is described. However, adjustments can be made by the above-described method even for other cases.

Although, adjustments are carried out with reference to the crosstalk amount Q, whether or not crosstalk occurs can be determined on the basis of tomographic images shown in FIG. 2C by displaying the tomographic images for the respective interference lights. If crosstalk occurs, the images are displayed as being provided with information differing from that of actual images. In this case, d1 and d3 are adjusted in the direction in which they are increased with the adjusting screws.

Figure 8B:
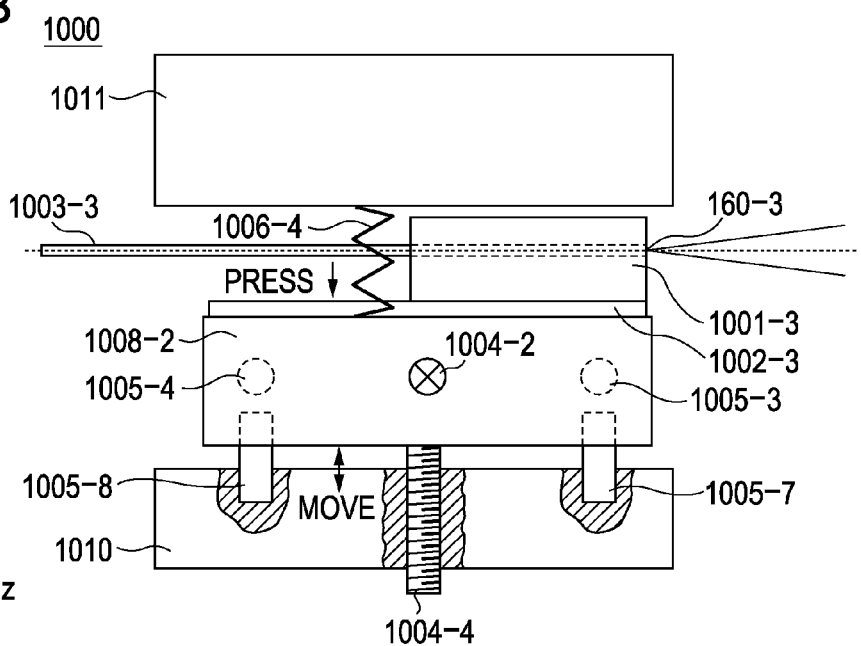

The fiber adjusting mechanism according to the embodiment is formed so that, as shown in FIG. 8B, the relative positions of the fiber ends 160-1 and 160-3 can be adjusted with respect to the fiber end 160-2 in the x direction. A side of the fiber end 160-3 will be described. A guide section, where pins 1005-7 and 1005-8 are inserted in a y guide member 1008-2, is provided with respect to the pins 1005-7 and 1005-8 secured to the base 1010, and is movably held in the x direction. In addition, a spring 1006-4 is provided between the y guide member 1008-2 and a member 1011 secured to the base 1010. By this, the y guide member 1008-2 is pressed in the direction of an arrow (x direction or pressing direction). The base 1010 is provided with a threaded hole, and is provided with an adjusting screw 1004-4. The adjusting screw 1004-4 contacts the y guide member 1008-2, to position the y guide member 1008-2. By rotating the adjusting screw 1004-4, the distance between the y guide member 1008-2 and the base 1010 can be changed, as a result of which the relative positions of the fiber ends 160-2 and 160-3 in the x direction can be adjusted. By also providing a similar structure to a side of the fiber end 160-1, the relative positions of the fiber ends 160-1 and 160-2 in the x direction can also be adjusted. As with the mechanism for adjusting d1 and d3, by such a mechanism, when assembling a device, initial adjustments in the x direction can be performed.

By providing the adjusting mechanism for making adjustments in the x direction, the straightnesses of the fiber ends 160-1 to 160-3 can be adjusted. FIG. 9C shows a case in which the intensity of the interference light 142-3 changes with time. The intensity of the interference light 142-3 is a value that is less than that of an initial state (shown by an alternate short and long dash line). From the straight line formed by the fiber ends 160-1 and 160-2, only the line of the fiber end 160-3 is shifted in the x direction. As with the adjustments of d1 and d3, it is possible to display the distributions of the intensities of the interference lights on a monitor (not shown), rotate the fiber end 160-3 with the adjusting screw 1004-4, and adjust the intensity so as to approach the intensity of the initial state.

Figure 10A:
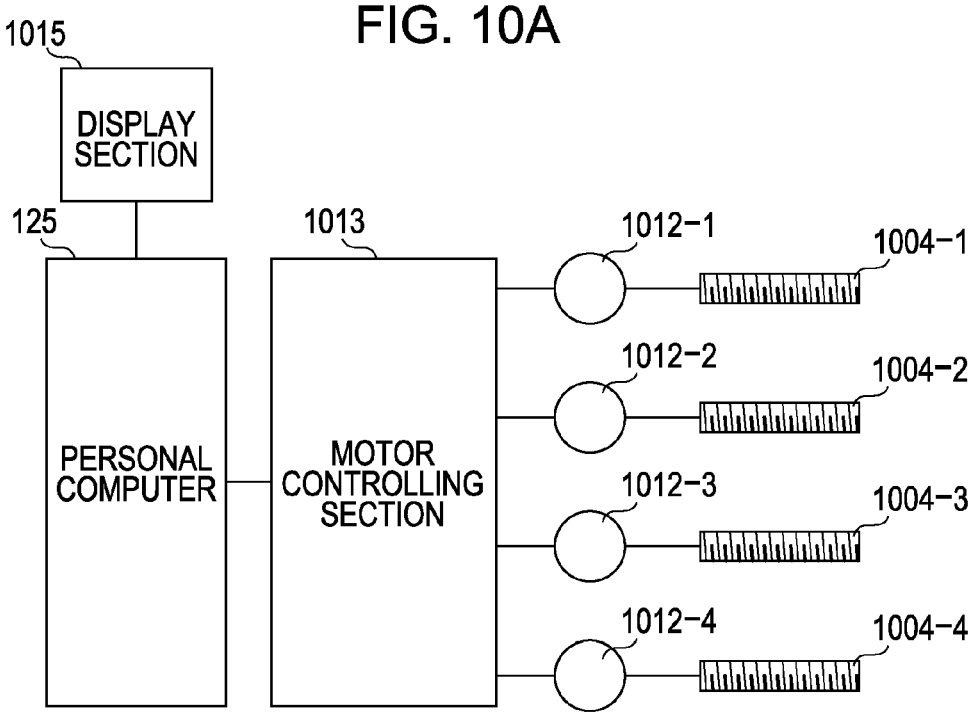
FIGS. 10A and 10B illustrate adjustments of the fiber ends in the fourth embodiment.

The rotation of the adjusting screws 1004 for adjusting the x and y directions mentioned up until now may be performed with a motor. FIG. 10A shows a block diagram. Reference numerals 1004-1 to 1004-4 denote the adjusting screws. Reference numerals 1012-1 to 1012-4 denote motors mechanically connected to the adjusting screws 1004-1 to 1004-5. Reference numeral 1013 denotes a motor controlling section. Reference numeral 125 denotes the computer. Reference numeral 1015 denotes a display section. By displaying the distributions of the intensities of the interference lights on the display section 1015 and by controlling the motor with, for example, a button for performing a displaying operation on the display section 1015 or a joy stick (not shown) provided at the motor controlling section 1013, it is possible to rotate the adjusting screws 1004-1 to 1004-4 to adjust the fiber ends 160-1 and 160-3.

Figure 10B:
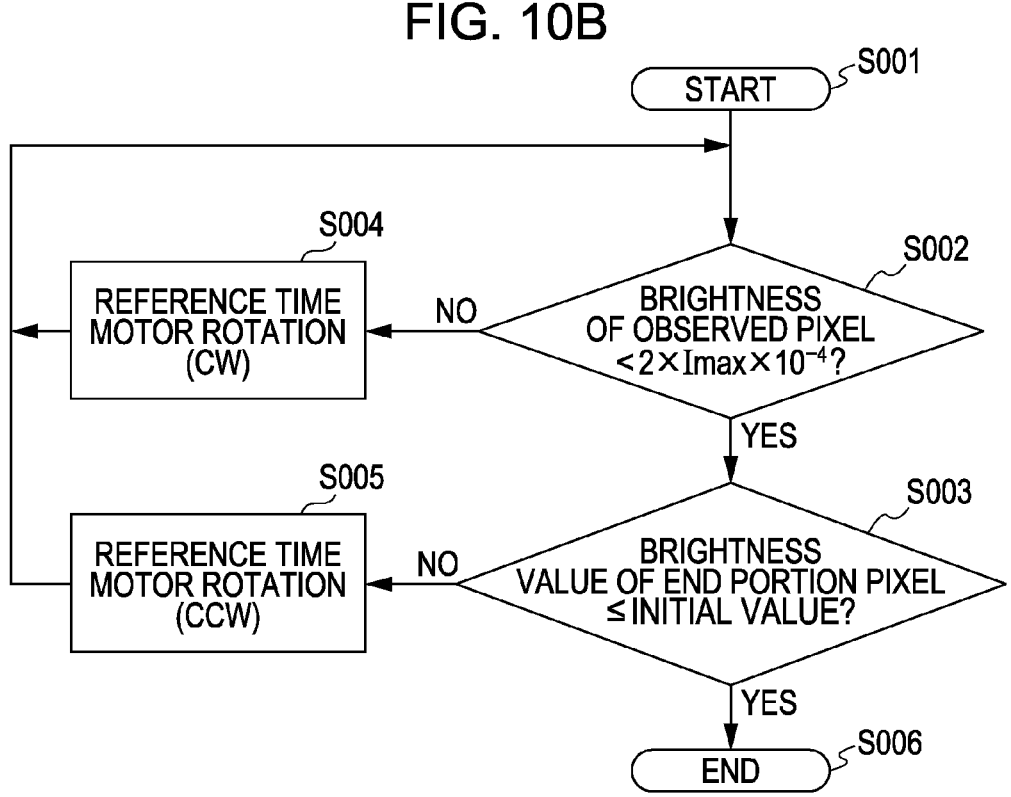

Further, automatic adjustment can be carried out. FIG. 10B shows a flowchart. In the flowchart, the procedure for adjusting d1 is described as an example.

In Step S001, an adjustment is started.

In Step S002, the intensity of a crosstalk evaluation pixel that is observed and that is generated on the line sensor 139 is compared with the aforementioned guide line value of $2 \times I_{max} \times 10^{-4}$. The crosstalk evaluation pixel is a pixel where the light having a wavelength of 781 nm of the combined light 142-2 that generates the aforementioned maximum crosstalk in the first embodiment is positioned at an initial state. As shown in FIG. 9A, when the intensity of this pixel is greater than or equal to the guide line value, the process proceeds to Step S004. If it is less than the guide line value, the process proceeds to Step S003.

In Step S004, the motor 1012-1 for adjusting d1 is rotated in a CW direction. Here, the CW direction of rotation of the motor 1012-1 is defined as a direction in which d1 is increased, and the motor is a DC motor. The motor moves for a time (reference time) in which the fiber end 160-1 moves by a small step (for example, on the order of 2 μm) for adjustments. Thereafter, the process proceeds to Step S002 to compare the intensity and the guide line value again.

In Step S003, the value of the intensity of a line-sensor end portion pixel at a side of the interference light 142-1 is compared with an initial state value at the same intensity. If the intensity value is greater than the initial state value, the process proceeds to Step S005, whereas, if the intensity value is less than the initial state value, the process proceeds to Step S006.

In Step S005, the motor 1012-1 for adjusting d1 is rotated in a CCW direction. Here, the CCW direction of rotation of the motor 1012-1 is defined as a direction in which d1 is reduced. The motor moves for the time (reference time) in which the fiber end 160-1 moves by a small step (for example, on the order of 2 μm) for adjustments. Thereafter, the process proceeds to Step S002 to compare the intensity and the guide line value again.

In Step S006, the adjustment ends.

It is possible to separately provide a timer for measuring an adjustment time from the Step S001, to display an error when the positional adjustment takes too much time.

The flowchart only shows the case in which d1 is adjusted. The same flowchart can be used for adjusting d3. It is also possible to carry out automatic adjustment in the x direction by comparing the maximum intensity of each interference-light area on the line sensor with the initial state value.

As described above, in the embodiment, by providing a mechanism that can adjust the fiber-end distances d1 and d3, it is possible to prevent the occurrence of crosstalk even if changes occur with time. Here, an example in which an adjusting mechanism is provided as a modification of the first embodiment is described. However, by providing a fiber-end adjusting mechanism to the structure according to the second embodiment or to the structure according to the third embodiment, it is possible to obtain similar effects.

Other Embodiments

The present invention is not limited to the details of the specific structures discussed in the embodiments. Therefore, obviously, some of the structural requirements may be modified within a range not departing from the scope of the present invention.

For example, although, in the third embodiment, the spectroscope is configured to disperse three combined lights in the y direction, three combined lights in the x direction, and three combined lights in the y-and-x direction, any number of combined lights may be used. If an odd number of combined lights is used, it is desirable that one of the lights be disposed so as to be aligned with the optical axis, as in the first to third embodiments. However, the present invention is not limited thereto. If an even number of combined lights is used, the influence of optical aberrations, diffraction efficiency, and diffraction angles can be made the same, so that it is desirable that the combined lights be symmetrical to the optical axis.

Although, in each of the above-described embodiments, the dispersing structure is one in which a plurality of fiber ends 160 for the spectroscope are disposed in the y direction and the x direction, the dispersing structure may be one in which the fiber ends 160 are inclined with respect to the axes. In particular, it is effective to incline them in the x direction. If the distance between the line sensors of the line sensor array 139A becomes small, and the fiber ends cannot be shortened to the distance prescribed by the magnification, they are formed so that an X component is essentially shortened by inclining the fiber ends.

As described above, according to the embodiments, it is possible to make measurements at a high speed and to reduce to size of the device. In addition, by forming the device so that crosstalk does not occur on a line sensor, it is possible to take a tomographic image of an examination object having reduced image quality degradation compared to that when a single measurement is conducted. Further, it is possible to bring the combined lights on the line sensor close to each other up to a level in which noise of tomographic images caused by crosstalk on the line sensor is inconspicuous.

Other Embodiments

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer, for example, via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-124274, filed May 22, 2009, and Japanese Patent Application No. 2010-082803, filed Mar. 31, 2010, which are hereby incorporated by reference herein in their entirety.

The invention claimed is:

1. An imaging apparatus using optical coherence tomography, the imaging apparatus comprising:
   a light source configured to generate light;
   first to fourth optical fibers;
   a splitting unit for splitting the light from the light source into first and second reference lights and first and second measuring lights guided in the first to fourth optical fibers, respectively;
   a scanning optical unit for scanning an examination object with the first and second measuring lights;
   a combining unit for combining the first reference light and the first measuring light returning from the examination object to a first combined light and for combining the second reference light and the second measuring light returning from the examination object to a second combined light, the first and second measuring lights irradiating different areas of the examination object in the direction intersecting with an optical axis of an optical path;
   a detecting unit for detecting the first and second combined lights, wherein the detecting unit includes a single dispersing element and a sensor, the single dispersing element being configured to disperse the first and second combined lights and disposed so that the first and second combined lights are incident on the single dispersing element at different incident angles, the sensor being configured to detect the first and second combined lights that have been dispersed by the dispersing element, wherein the sensor includes a first area and a second area, and an illuminating unit for illuminating the first area and the second area by the dispersed first combined light and the dispersed second combined light, respectively, comprising:

fifth and sixth optical fibers, wherein the first and second combined lights are guided in the fifth and sixth optical fibers to their exit ends, respectively, wherein a distance between the first area and the second area is based on a distance between the exit ends of the fifth optical fiber and the sixth optical fiber and an optical magnification at the detecting unit.

2. The imaging apparatus using the optical coherence tomography according to claim 1, wherein the first area and the second area are disposed in the direction of the dispersion, and wherein a pixel at a side of the first area is disposed in the second area is so as to be included in an area of the sensor where, of the light that is focused at the first area, light having an intensity that is lower than $10^{-4}$ times an intensity of the light detected at the second area is detected.

3. The imaging apparatus using the optical coherence tomography according to claim 1, wherein the first area and the second area are disposed in the direction of the dispersion, wherein the sensor includes a third area disposed substantially perpendicularly to the direction of the dispersion with respect to the first area, and wherein a distance between the first area and the third area is less than the distance between the first area and the second area.

4. The imaging apparatus using the optical coherence tomography according to claim 3, wherein the sensor is a line sensor provided so as to extend from the first area to the third area.

5. The imaging apparatus using the optical coherence tomography according to claim 1, further comprising an adjusting mechanism for adjusting a distance between the first area and the second area by adjusting a distance between a fiber end of the fifth optical fiber and a fiber end of the sixth optical fiber from where the first and second combined lights exit, respectively, taking into account an optical magnification of the first and second combined lights between the fiber ends of the fifth and sixth optical fibers and the sensor.

6. The imaging apparatus according to claim 1, comprising a single dispersion element wherein the single dispersion element is a transmission dispersing unit.

7. The imaging apparatus according to claim 1, further comprising:

an obtaining unit for obtaining an optical coherence tomographic image of the examination object based on the first and second combined lights detected at the sensor.

8. The imaging apparatus according to claim 1, wherein the splitting unit is adapted to split the light into more than two reference lights including the first and second reference lights and more than two measurement lights including the first and second measurement lights;

the combining unit is adapted to combine respective ones of the more than two reference lights and measurement lights into respective more than two combined lights including the first and second combined lights;

the detection unit is configured to detect the more than two combined lights;

the dispersing unit is configured to disperse the more than two combined lights;

the sensor is configured to detect the more than two combined lights having been disposed by the dispersing element and includes more than two areas disposed in the direction of the direction of dispersion and/or perpendicular to the direction of the dispersion; and the illuminating unit is configured to illuminate the more than two dispersed lights to the respective more than two areas, respectively.

9. The imaging device according to claim 8, wherein the sensor is configured to detect the more than two combined lights having been disposed by the dispersing unit and includes more than two areas disposed in the direction of the direction of dispersion and perpendicular to the direction of the dispersion; and the illuminating unit is adapted to perform the illumination so that the plurality of combined lights of the direction of the dispersion intersect at the single dispersing element with the combined lights of the direction perpendicular to the dispersing unit.

10. The imaging apparatus according to claim 1, wherein the combining unit is arranged such that the dispersing unit is illuminated with the first and second combined lights at an incident angle at which the illumination areas have different areas.

11. The imaging apparatus according to claim 1, wherein the combining unit is arranged such that the dispersing unit is illuminated with the plurality of first and second combined lights at an incident angle at which the dispersion efficiency of the dispersion unit is substantially a maximum.

12. The imaging apparatus according to claim 1, wherein the examination object is a subject's eye.

13. A method comprising:

generating light;

splitting the light into first and second reference lights, and first and second measuring lights;

scanning an examination object with the first and second measuring lights;

combining the first reference light and the first measuring light returning from the examination object into a first combined light; and combining the second reference light and the second measuring light returning from the examination object into a second combined light, the first and second measuring lights irradiating different areas of the examination object in the direction intersecting with an optical axis of an optical path;

dispersing the first and second combined lights; and detecting the first and second combined lights with a detecting unit including a single dispersing element and a sensor, the single dispersing element being configured to disperse the first and second combined lights and disposed so that the first and second combined lights are incident on the single dispersing element at different incident angles, the sensor being configured to detect the first and second combined lights that have been dispersed by the dispersing element, the sensor including a first area and a second area;

wherein the first and second combined lights are guided in a first optical fiber and a second optical fiber to their exit ends, respectively, and a distance between the first area and the second area is based on a distance between the exit ends of the first optical fiber and the second optical fiber and an optical magnification between the exit ends and the sensor.

14. The method according to claim 13, further comprising adjusting a distance between the first area and the second area by adjusting a distance between a first fiber end of the first optical fiber and a second fiber end of the second optical fiber from where the first and second combined lights, respectively, exit before they are dispersed, taking into account an optical magnification of the first and second combined lights between the first and second fiber ends and the sensor.

15. A non-transitory computer readable storage medium having stored thereon a program wherein a computer is caused to execute an imaging method according to claim 13.

16. An imaging apparatus comprising:
a single dispersing element configured to disperse a plurality of combined lights formed by combining a plurality of returning lights and a plurality of reference lights, the plurality of returning lights returning from an examination object illuminated with a plurality of measuring lights, the plurality of reference lights respectively corresponding to the plurality of measuring lights, the plurality of measuring lights irradiating different areas of the examination object in the direction intersecting with an optical axis of an optical path;
an illumination unit configured to illuminate the single dispersing element with the plurality of combined lights so that the plurality of combined lights are incident on the single dispersing element at different incident angles;
a sensor configured to detect the dispersed plurality of combined lights; and
an obtaining unit configured to obtain an optical coherence tomographic image of the examination object based on the detected plurality of combined lights.

17. The imaging apparatus according to claim 16,
wherein the sensor detects the dispersed plurality of lights at a plurality of areas included in the sensor, and
wherein the illumination unit, the single dispersing unit, and the sensor are disposed so that, when a part of a first combined light detected at a first area of the plurality of areas is detected at a second area, a light amount of the part of the first combined light detected at the second area is lower than $10^{-4}$ times a light amount of a second combined light detected at the second area.

18. The imaging apparatus according to claim 16, wherein the examination object is a subject's eye.

19. An imaging apparatus comprising:
a plurality of optical fibers configured to guide a plurality of combined lights formed by combining a plurality of returning lights and a plurality of reference lights, the plurality of returning lights returning from an examination object illuminated with a plurality of measuring lights, the plurality of reference lights respectively corresponding to the plurality of measuring lights, the plurality of measuring lights irradiating different areas of the examination object in the direction intersecting with an optical axis of an optical path;
a single dispersing element configured to disperse the plurality of combined lights emitted from fiber ends of the plurality of optical fibers, the single dispersing element being disposed so that the emitted plurality of combined lights are incident on the single dispersing element at different incident angles; and
a sensor configured to detect the dispersed plurality of combined lights.

20. The imaging apparatus according to claim 19,
wherein the sensor detects the dispersed plurality of lights at a plurality of areas included in the sensor, and
wherein the plurality of optical fibers, the single dispersing unit, and the sensor are disposed so that, when a part of a first combined light detected at a first area of the plurality of areas is detected at a second area, a light amount of the part of the first combined light detected at the second area is lower than $10^{-4}$ times a light amount of a second combined light detected at the second area.

21. The imaging apparatus according to claim 19, wherein the examination object is a subject's eye.

* * * * *